(12) United States Patent
Heaton, II et al.

(10) Patent No.: US 11,672,519 B1
(45) Date of Patent: *Jun. 13, 2023

(54) RETRACTOR SYSTEMS WITH CLOSED LOOP CONTROL

(71) Applicant: ViOptix, Inc., Newark, CA (US)

(72) Inventors: Larry C. Heaton, II, Pleasanton, CA (US); Alex Keller, Manhasset, NY (US); Robert E. Lash, Redwood City, CA (US); Jimmy Jian-min Mao, Fremont, CA (US)

(73) Assignee: ViOptix, Inc., Newark, CA (US)

( * ) Notice: Subject to any disclaimer, the term of this patent is extended or adjusted under 35 U.S.C. 154(b) by 147 days.

This patent is subject to a terminal disclaimer.

(21) Appl. No.: 16/897,217

(22) Filed: Jun. 9, 2020

Related U.S. Application Data

(60) Continuation of application No. 15/585,083, filed on May 2, 2017, now Pat. No. 10,675,013, which is a
(Continued)

(51) Int. Cl.
*A61B 17/02* (2006.01)
*A61B 5/1455* (2006.01)
(Continued)

(52) U.S. Cl.
CPC ...... *A61B 17/0206* (2013.01); *A61B 5/14542* (2013.01); *A61B 5/14552* (2013.01); *A61B 17/02* (2013.01); *A61B 17/025* (2013.01); *A61B 2017/00022* (2013.01); *A61B 2017/00057* (2013.01); *A61B 2017/00084* (2013.01);
(Continued)

(58) Field of Classification Search
CPC ....... A61B 17/02; A61B 17/025; A61B 5/145; A61B 5/14542
See application file for complete search history.

(56) References Cited

U.S. PATENT DOCUMENTS

| | | | |
|---|---|---|---|
| 4,784,150 A | | 11/1988 | Voorhies et al. |
| 4,945,896 A | * | 8/1990 | Gade ................ A61B 5/14553 600/206 |

(Continued)

OTHER PUBLICATIONS

D. Hueber et al., "New Optical Probe Designs for Absolute (Self-Calibrating) NIR Tissue Hemoglobin Measurements," Proceedings of Optical Tomography and Spectroscopy of Tissue III, Jan. 1999, 618-631, vol. 3597.

(Continued)

*Primary Examiner* — Christopher J Beccia
(74) *Attorney, Agent, or Firm* — Aka Chan LLP

(57) ABSTRACT

A retractor system with a closed loop control includes a retractor having one or more sensors, which measure parameters associated with a retracted tissue. The system further includes a positioning mechanism connected to the retractor and a controller which receives feedback signals from the sensors. Based on the feedback signals from the sensors, the retractor is actuated by the positioning mechanism so that the tissue can be retracted while maintaining the parameters associated with the retracted tissue above a threshold level or within a desired range. Another retractor system includes a retractor with a force sensor and at least one additional sensor, which can be used without a closed loop control arrangement.

32 Claims, 17 Drawing Sheets

Related U.S. Application Data division of application No. 12/365,716, filed on Feb. 4, 2009, now Pat. No. 9,636,096.

(51) Int. Cl.
  *A61B 5/145* (2006.01)
  *A61B 90/00* (2016.01)
  *A61B 90/30* (2016.01)
  *A61B 17/00* (2006.01)

(52) U.S. Cl.
  CPC ........... *A61B 2017/00119* (2013.01); *A61B 2017/00398* (2013.01); *A61B 2017/0256* (2013.01); *A61B 2017/0262* (2013.01); *A61B 2090/032* (2016.02); *A61B 2090/065* (2016.02); *A61B 2090/306* (2016.02)

(56) References Cited

U.S. PATENT DOCUMENTS

| | | | |
|---|---|---|---|
| 5,088,493 A | | 2/1992 | Giannini et al. |
| 5,529,571 A | * | 6/1996 | Daniel ............... A61B 17/0206 600/218 |
| 5,584,296 A | | 12/1996 | Cui et al. |
| 5,807,377 A | | 9/1998 | Madhani et al. |
| 5,879,294 A | | 3/1999 | Anderson et al. |
| 6,078,833 A | | 6/2000 | Hueber |
| 6,285,904 B1 | | 9/2001 | Weber et al. |
| 6,452,354 B1 | | 9/2002 | Ellsworth et al. |
| 6,487,343 B1 | | 11/2002 | Lewandowski et al. |
| 6,516,209 B2 | | 2/2003 | Cheng et al. |
| 6,549,284 B1 | | 4/2003 | Boas et al. |
| 6,587,703 B2 | | 7/2003 | Cheng et al. |
| 6,597,931 B1 | | 7/2003 | Cheng et al. |
| 6,708,048 B1 | | 3/2004 | Chance |
| 6,735,458 B2 | | 5/2004 | Cheng et al. |
| 6,892,006 B2 | | 5/2005 | Lewandowski et al. |
| 7,185,590 B2 | | 3/2007 | Fu et al. |
| 7,226,413 B2 | | 6/2007 | McKinley |
| 7,254,427 B2 | | 8/2007 | Cho et al. |
| 7,355,688 B2 | | 4/2008 | Lash et al. |
| 7,435,219 B2 | | 10/2008 | Kim |
| 10,675,013 B1 | * | 6/2020 | Heaton, II ......... A61B 5/14542 |
| 2004/0111016 A1 | | 6/2004 | Casscells et al. |
| 2008/0045822 A1 | | 2/2008 | Phillips et al. |
| 2008/0319290 A1 | | 12/2008 | Mao et al. |
| 2009/0018401 A1 | * | 1/2009 | Kim ................... A61B 17/0293 600/210 |

OTHER PUBLICATIONS

A. Balakrishnan et al., "Smart Retractor for Use in Image Guided Neurosurgery", 2003 Summer Bioengineering Conference, Jun. 25-29, 2003, Sonesta Beach Resort in Key Biscayne, Florida, pp. 895-896.

* cited by examiner

RETRACTOR SYSTEMS WITH CLOSED LOOP CONTROL

CROSS-REFERENCE TO RELATED APPLICATIONS

This patent application is a continuation of U.S. patent application Ser. No. 15/585,083, filed May 2, 2017, issued as U.S. Pat. No. 10,675,013 on Jun. 9, 2020, which is a divisional of U.S. patent application Ser. No. 12/365,716, filed Feb. 4, 2009, issued as U.S. Pat. No. 9,636,096 on May 2, 2017. These applications are incorporated by reference.

BACKGROUND OF THE INVENTION

This invention relates to the field of medical devices and more specifically to a tissue retractor with a sensor.

Retractors play an important role in medicine. Retractors retract or hold aside tissues (e.g., nerve root, spinal cord, facial nerve, muscle, liver, kidney, and others) so that a surgeon can gain access to an area for operation or observation. There are a variety of retractors for different tissue types. All retractors physically contact a tissue and typically apply a certain amount of pressure to the tissue at the point of contact during retraction.

It is important that retracted tissues are not damaged during retraction. With current retractors, however, it is difficult, if not impossible, to tell whether the tissues are being damaged during the retraction. Damage to any tissue can be devastating, which can result in diminished or loss of its function or pain. For example, damage to nerve root or any nerve is undesirable, leading to loss of sensation, numbness, or pain to the patient.

There is, then, a continuing demand for retractors and other medical devices that can perform their function without damaging retracted tissues. It would also be desirable to develop retractors and medical devices that provide patient feedback, provide more features, are easier to use, and generally address the needs of patients, doctors, and others in the medical community.

Therefore, there is a need to provide improved systems and techniques for retractors.

BRIEF SUMMARY OF THE INVENTION

In one aspect of the invention, the retractor system for retracting a tissue has a closed loop control system. The retractor system includes a retractor having a sensor. The retractor system also includes a positioning mechanism which is connected to the retractor. The retractor system further includes a controller which is connected to the sensor and the positioning mechanism. The sensor measures some parameter that reflects the health or condition of a retracted tissue, and the parameter is transmitted as an input signal to the controller. The controller generates a control signal to control movement of the positioning mechanism based on the input signal from the sensor. The retractor in turn moves according to movement of the positioning mechanism.

The control signal from the controller actuates the retractor, through movement of the positioning mechanism, if the input signal from the sensor does not meet a threshold level or is not within a desired range. In other words, a retraction force applied to the retractor and a retraction distance of a tissue are adjusted based on the input signal from the sensor. The system can continuously monitor the parameter measured by the sensor and can adjust a retraction force applied to the retractor so that the parameter of the retracted tissue can be maintained above a threshold level or within a desired range.

In one embodiment, the retractor system includes a retractor having an oximeter sensor. The oximeter sensor measures oxygen saturation level of a retracted tissue. During surgery, it is desired that oxygen saturation level of a retracted tissue remains above a certain level so that the retracted tissue does not suffer hypoxia. The oximeter sensor can continuously monitor oxygen saturation level of the retracted tissue, and this information can be transmitted to the controller. The controller compares the measured oxygen saturation to a desired oxygen saturation level for the tissue. The system can then make an appropriate adjustment to a retraction force applied to the retractor so that the oxygen saturation level of the retracted tissue returns to above the certain level or within a desired range.

In another embodiment, the retractor system includes a nerve retractor having a sensor. A nerve retractor has a sensor at its tip, which is used to contact and pull aside a nerve. The sensor can measure various parameters of a retracted nerve, including an oxygen saturation level, temperature, color, and others. In one implementation of the invention, the sensor has at least one source structure including a fiber optic cable and at least one detector structure including a fiber optic cable.

In another embodiment, the retractor system further includes a force sensor which is connected to a retractor and a positioning mechanism. The force sensor measures a force applied to a tissue by a tip of the retractor when the positioning mechanism alters a position of the retractor. The force applied to the tissue can be continuously monitored and can be used as another input signal for the controller to determine a control signal for controlling movement of the positioning mechanism.

In another embodiment, a method includes determining a parameter of a tissue that is retracted by a retractor using a sensor which is connected to the retractor, determining if the parameter is above a first value, and producing a control signal to alter a position of the retractor if the parameter is not above a first value. In some embodiments, the method further includes determining if the parameter is below a second value, where the second value is greater than the first value, and producing a control signal to alter a position of the retractor if the parameter is not below the second value. These method steps can be continuously repeated to maintain the parameter of a retracted tissue above the first value or between the first value and the second value.

In another aspect of the invention, the retractor system can be used without a closed control loop arrangement. The retractor system has a retractor including a shaft having a proximal end and a distal end, a tip connected to the distal end of the shaft, where the tip has a retractor portion and an oximeter sensor. The retractor system also includes a force sensor connected to, in, contained within, or part of the retractor. The retractor system further includes a system unit that has a display, processor, signal emitter circuit, and signal detector circuit. The retractor system can further include a receptacle for connecting optical fibers.

In one implementation of the system, the retractor system has an oximeter sensor including a first sensor opening and a second sensor opening on a bottom side of the tip. There is a first optical fiber and a second optical fiber. The first optical fiber passes through a channel in the shaft and a distal end of the first optical fiber is connected to a first sensor opening of the tip. The second optical fiber passes through the channel in the shaft and a distal end of the second optical fiber is connected to a second sensor opening of the tip.

Embodiments of the invention can be applied to retract any tissue. In one implementation, the retractor system includes a nerve retractor to retract a nerve tissue, such as a spinal cord, nerve root, facial nerve, peripheral nerve and others. In another implementation, the retractor system includes an organ retractor of varying shape and size to retract a liver, kidney, lung, stomach, intestine, uterus, ovary, bladder, brain, and others.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
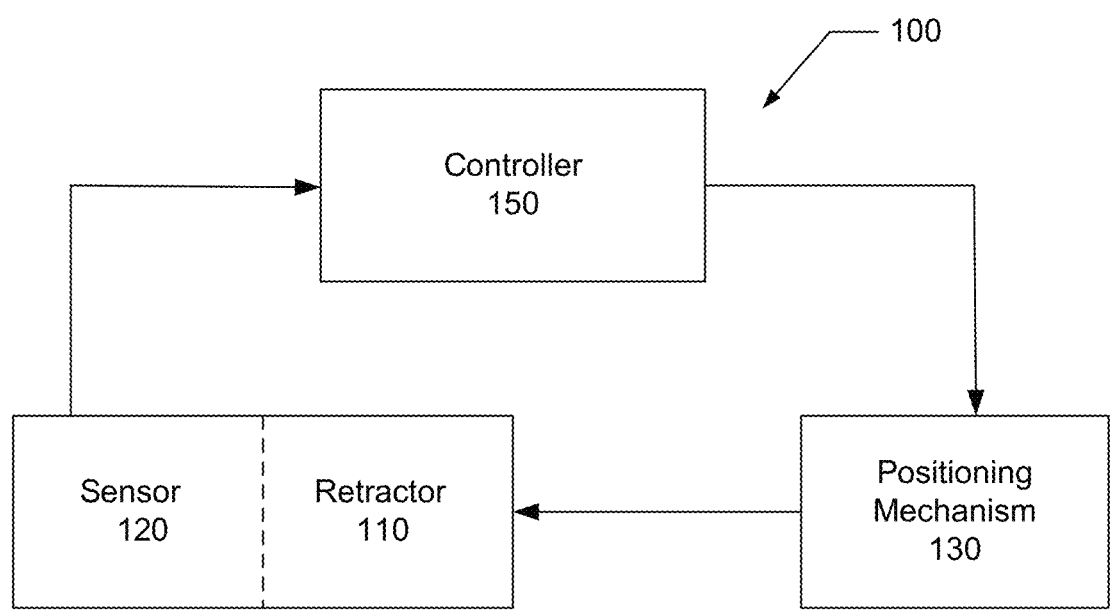
FIG. 1 shows a block diagram of a retractor system including a closed loop control system. The system has a retractor for retracting a tissue, where the retractor includes sensor for measuring a parameter of the tissue so that the parameter of the tissue can be maintained above a threshold level or within a desirable range.

During surgery a tissue that needs to be operated on is sometimes buried underneath or concealed by another tissue in a body. In such a circumstance, tissue retractors can be used to expose the surgical site. However, when the retractors are handled and adjusted by hand, it is difficult for the surgeon to determine how much force the retractors are applying on the tissue. For example, when a retractor is pulling a nerve, it may be compressing the nerve with too much force at the point of contact or it may be crushing a blood vessel (e.g., blood vessels bundled with the nerve) or other vital surrounding tissues.

The surgical retraction can result in a structural damage to the tissue or tissue ischemia due to lack of blood flow. Tissue ischemia caused by retraction or local trauma can be particularly devastating if the damaged tissue involves a nervous system. The additive force of surgical retraction may further damage a nerve tissue that has already been compromised. An abrupt decrease in blood flow to a nerve tissue can result in permanent sensory or motor deficit or both. For example, by depriving sufficient blood flood through the nerve caused by the retraction, the nerve may be deprived of oxygen. With insufficient oxygen, the nerve may die or be partially damaged. The amount of time the nerve has been retracted may also be a factor in whether it will be damaged.

The retractor system in accordance with the present invention allows the surgeon to monitor the condition of a retracted tissue in real time, while retracting the tissue. Typically, one or more parameters that reflect the condition of a retracted tissue are measured during retraction. If the measured parameters indicate that the condition of the retracted tissue is deteriorating, a corrective measure can be taken immediately during surgery to improve the condition of the retracted tissue. Accordingly, any potential damage to the retracted tissue can be minimized.

In embodiments of the invention, a retractor system includes a retractor having one or more sensors, which are connected to, in, contained within, or part of the retractor. The sensors can measure parameters of the tissue while being retracted. Based on the measured parameters, the retractor system can adjust a retraction force applied to a tip of the retractor so that certain parameters of the tissues can be maintained above a threshold level or within a desired range. For example, the parameters that can be measured by the sensors include oxygen saturation level of the retracted tissue, tissue temperature, tissue color, and others.

In one implementation, a retractor includes an oximeter sensor. When a tissue being retracted is compressed with too much force, then blood flow to the retracted tissue will diminish and the tissue oxygen saturation level may decrease. The oximeter sensor can measure oxygen saturation level of the retracted tissue, and this information can be transmitted to a controller in the system so that a retraction force applied to the retractor tip can be adjusted. The oxygen saturation level or other measurable parameters can be continuously monitored during retraction so that stress on the retracted tissue can be minimized.

In another implementation, a retractor device or system includes a force sensor and an oximeter sensor, and can be used without closed loop control arrangement. Thus, the retractor device and system can simultaneously measure two parameters of a retracted tissue-oxygen saturation level of the retracted tissue contacting the tip of the retractor device and an amount of force applied to the retracted tissue by the tip. By having both oximeter sensor and force sensor, the retractor device can better assist determining the effect of surgical manipulation on the health of nerve roots and other tissues.

Embodiments of the present invention provide several advantages. By providing various feedback signals measured from one or more sensors to the controller, the oxygen saturation level or other measurable parameters of a retracted tissue can be maintained above a threshold level or within a desired range without large fluctuations during surgery. A retraction distance and retraction force can also be automatically and continuously adjusted, as necessary or desired, during a surgical procedure. Since corrective measures are taken immediately during surgery, any damage to a retracted tissue can be minimized. Furthermore, in some embodiments, since movement of the retractor system is controlled mechanically, it eliminates a concern over the surgeon's hand tremor negatively impacting the surgery.

Aspects of the invention can be embodied in retractors of any type and for any purpose. For example, these include retractors for a spinal cord, nerve root, peripheral nerve, facial nerve, brain, muscle, connective tissue, liver, kidney, uterus, ovary, stomach, intestine, bladder, bone, prostate, thyroid, parathyroid, adrenal gland, pancreas, spleen, heart, and others, and combinations of these. These retractors retract tissue, organs, and other parts of the body (or body parts). For this application, "tissue" and "organ" are used interchangeably to refer to any body part or aggregate of cells. In other words, "tissue" may be used to refer to an organ, and vice versa.

Examples of embodiments of the invention are illustrated using figures and are described below. The figures described herein are used to illustrate embodiments of the invention, and are not in any way intended to be restrictive of the broad invention. Embodiments of the invention are not limited to the specific arrangements and constructions shown and described. For example, features shown in one figure can be combined with other features shown in another figure.

FIG. 1 illustrates a block diagram of a system 100 that has a closed loop control arrangement. System 100 includes a retractor 110 which is used to retract a tissue. Retractor 110 includes a sensor 120. System 100 also includes a positioning mechanism 130 which is connected to retractor 110. The positioning mechanism adjusts a position of the retractor so that a tip of the retractor can retract or hold aside a tissue to a desired location, allowing the surgeon to gain access the surgical site. When the tissue is pulled or retracted by the retractor through movement of the positioning mechanism, a certain amount of force is applied to a tip of the retractor (and also on the tissue). This force is referred to as "retraction force."

System 100 also includes a controller 150. Controller 150 receives an input signal from sensor or transducer 120 which measures a parameter associated with the retracted tissue. Based on the input signal from the sensor, the controller produces a control signal which controls movement of positioning mechanism 130. In turn, the positioning mechanism adjusts a position of the retractor. The system can continuously monitor the parameter measured by the sensor and adjust a retraction force applied to the retractor so that the parameter of the retracted tissue can be maintained above a first threshold level, below a second threshold level (different from the first), or within a desired range.

In one embodiment of the invention, sensor 120 is an oximeter sensor, which is connected to, in, contained within, or part of retractor 110. The oximeter sensor measures an oxygen saturation value of a retracted tissue. This information is transmitted to controller 150. The controller compares the measured oxygen saturation value of the retracted tissue to a predetermined oxygen saturation level or range that the user desires to maintain during retraction.

For example, during surgery a tissue may be retracted to a given distance by a retractor to expose a surgical site, and the surgeon may desire to maintain an oxygen saturation value of the retracted tissue between about 30 and 45 percent to avoid hypoxia and damage to the tissue. During surgery, if the measured oxygen saturation of the retracted tissue is within 30 to 45 percent, then the retractor may hold aside the tissue at the given distance with a constant retraction force. However, if the measured oxygen saturation of the retracted tissue goes below or above the predetermined 30 to 45 percent range, then the retraction force applied to a tip of the retractor can be adjusted so that the oxygen saturation value of the retracted tissue returns back to the predetermined 30 to 45 percent range.

During surgery, a desire for maintaining a relatively healthy oxygen saturation level for a retracted tissue is balanced against a need to retract the tissue to a distance that is desired (may be referred to as an "initially selected distance") to expose the surgical site. Typically, the tissue is initially retracted to an initially selected distance by a retractor, and the oxygen saturation level of the retracted tissue is monitored. If the oxygen saturation level of the retracted tissue falls below a threshold level, then the controller reduces a retraction distance to minimize stress on the retracted tissue. When the oxygen saturation level of the retracted tissue stabilizes and returns back to the threshold level, then the controller increases the retraction distance towards the initially selected distance so that the surgeon can readily access the surgical site.

In another embodiment, system 100 may include a different sensor in addition or in alternative to the oximeter sensor. For example, a force sensor can be included in the system. A force sensor is connected to both the retractor and the positioning mechanism so that the force sensor measures an amount of force that is applied to a tissue at the retractor tip by movement of the positioning mechanism. The amount of force that is applied to the retractor tip can be continuously monitored and can be used as another input signal for the controller to determine a control signal for controlling the positioning mechanism.

For instance, it may be determined from previous trials that when a certain amount of force is applied to a particular tissue during retraction, it can either break or damage the tissue. Then it is desirable that such a force is avoided in retracting the tissue even if an oxygen saturation value measured from the tissue may initially be within the desired oxygen saturation range. Such a force may be set as a threshold force value by the controller so that the positioning mechanism is prevented from applying the threshold force or any force larger than the threshold force.

A threshold force value may depend on many factors, such as tissue type, tissue size, temperature, and others. For example, a threshold force value for a delicate tissue such as a nerve root is typically lower than a threshold force value for a skeletal muscle. When the force sensor measures that a force applied to the retractor tip exceeds the threshold force value, then the controller sends a control signal to the positioning mechanism so that the positioning mechanism moves in a direction that reduces a retraction force applied to the retractor tip.

Any suitable force sensor can be used in embodiments of the invention. For example, a force sensor can be a strain gauge load cell. The load cell is a transducer that converts a force or load acting on it into an electrical signal. When there are changes in the force or load cell, there will be a change in the electrical signal. Through a mechanical arrangement, the force being sensed deforms a strain gauge along the axis of the load cell. The strain gauge converts the deformation into an electrical signal in proportion to the load. In embodiments of the invention, one end of the load cell can be attached to a retractor (e.g., at its handle) and the other end of the load cell can be attached to a positioning mechanism.

In another example, a force sensor can be a thin piezoresistive force sensor. The piezoresistive force sensor is constructed of two substrate layers of polyester and polyimide film. Each layer has a conductive material, such as silver and a layer of pressure-sensitive ink. Then an adhesive is used to laminate the two substrate layers, forming a force sensor. This piezoresistive force sensor is commercially available as FlexiForce® sensors from Tekscan (Boston, Mass.). The piezoresistive force sensor can be attached to a tip of a retractor (e.g., a retractor portion) which is used to contact and retract a tissue. When the tip of the retractor contacts and pulls aside a tissue, the pressure applied to the tissue by the retractor tip is directly measured by the piezoelectric force sensor at the point of contact.

Many other types of sensors can be connected to the retractor in embodiments of the invention. For example, a thermal sensor, position sensor, visual sensor such as a camera, and others may be used, in addition or in alternative to the previously mentioned sensors. Various sensors in embodiments of the invention can provide input signals to the controller so that an appropriate control signal can be generated by the controller to move the positioning mechanism and the retractor.

Retractor 110 in embodiments of the invention can be used to retract various tissue types. For example, a retractor can retract a nerve tissue (e.g., spinal cord, nerve root, facial nerve, peripheral nerve, and others), skeletal muscles, smooth muscles, nerve roots, connective tissues, brain, lungs, kidneys, liver, stomach, intestines, ovaries, uterus, bladder, bone, prostate, thyroid, parathyroid, adrenal gland, pancreas, spleen, heart, and others. The size and shape of a retractor will vary depending on the tissue type.

For example, a retractor for a skeletal muscle will be larger than a retractor for a nerve root. In one implementation of the invention, a retractor is a nerve retractor and a tissue to be retracted is a nerve root, spinal cord, facial nerve, or peripheral nerve. Structural and functional properties of a nerve root retractor are described more in detail below and in FIG. 5.

Positioning mechanism 130 in embodiments of the invention actuates retractor 110. A positioning mechanism can be a device that comprises one or more components, which are operatively linked together, and is capable of moving another object that is attached to its component. Movement of the positioning mechanism can be controlled by a control signal produced by a controller. In addition, the positioning mechanism can be controlled by a user input. For example, a component of the positioning mechanism can be operatively connected to a joystick or stylus so that the user can manually manipulate movement of the positioning mechanism.

In some embodiments, a positioning mechanism may include a macroactuation component to adjust a large movement of a retractor and a microactuation component for a fine tuning of a retractor. For example, the macroactuation component of the positioning mechanism can place a retractor at a proper height and X-Y coordinate relative to a tissue so that the retractor is ready to retract the tissue. The microactuation component of the positioning mechanism can be used to pull or retract the tissue according to a control signal provided by a controller.

In one implementation, a microactuation component of a positioning mechanism can include a linkage element connected to an actuator. In this embodiment, the linkage element is attached to a retractor. Thus, movement produced by the actuator is transferred to the linkage element, which in turn alters a position of the retractor.

A number of different types of linear actuators can be used in a positioning mechanism. These include a rotary motor with a lead screw, where the rotation of the motor rotates the screw, which in turn moves a linkage element attached to a nonmoving part of the rotary motor. Another type of actuator is a hydraulic actuator, where a hydraulic pressure displaces a hydraulic piston to achieve a linear movement. A pneumatic actuator can also be used, where air pressure displaces a piston to achieve a linear movement. These positioning mechanisms provide a range of motion in a single axis, in a forward and reverse direction.

In another implementation, a positioning mechanism may further include a macroactuation component to initially position a retractor at a proper location relative to a tissue to be retracted. For example, a platform with a height adjustable supporting post can be used to adjust the height of a retractor relative to a tissue to be retracted. The macroactuation component allows the user to adjust the height of a retractor mechanically and eliminates a concern over unsteady hands or hand tremor of the user affecting the control of the retraction system.

Other suitable positioning mechanisms can be included to control movement of a retractor in embodiments of the invention. For example, a planar magnetic levitation positioning system can be used. Typically, a planar magnetic levitation positioning system includes a levitated platform which is suspended with no support other than magnetic fields. A retractor can be attached to a levitated platform, and its positioning can be manipulated according movement of the levitated platform. This system provides a six-degree-of-freedom for a retractor, where the retractor can move forward/backward, up/down, left/right combined with rotation about three perpendicular axes. An example of a planar magnetic levitation positioning system is described in, for example, U.S. Pat. No. 7,185,590, which is incorporated by reference along with all other references cited in the application.

Another positioning mechanism suitable in embodiments of the invention includes a robotic arm described in, for example, U.S. Pat. No. 5,807,377, which is incorporated by reference. A retractor can be attached at one end of a robotic arm, and the retractor can be manipulated by movement of the robotic arm.

In embodiments of the invention, controller 150 includes several components to handle input and output signals. For example, the controller includes a memory that stores algorithms or codes necessary to process the input signals. The controller also includes a processor configured to rapidly execute the algorithms to produce a control signal to control movement of a positioning mechanism and a retractor.

The memory of the controller can be preloaded or preprogrammed with information regarding a desired or predetermined oxygen saturation value or range, threshold force, and others. The memory can also be preprogrammed with one or more lookup tables. For example, a lookup table may correspond to the recorded measurements from an oximeter sensor and contains a control signal request for the positioning mechanism appropriate for the detected oxygen saturation measurements. In another example, a lookup table may correspond to the recorded measurements from a force sensor and contains a command for a positioning system for the detected force measurements as determined by the force sensor.

The controller may include one or more user interface devices that enable the user to input data or various parameters. For example, the controller may include a keyboard or touch screen monitor that enables the user to input information into the controller regarding a patient, tissue type, desired or predetermined oxygen saturation value or range for a retracted tissue, threshold force values, and others. The controller may also include a voice recognition system that enables the user to input a command or data.

The controller may also include various output devices. For example, a controller may include a display panel. A display panel may be used to show a current oxygen saturation value of a retracted tissue, a retraction distance, or an amount of force that is applied to the retractor. The display panel can also display an elapsed time for retraction as well as data obtained at various time points. The controller may also include a speaker or an alarm. The user can be alerted with an audible signal if the condition of a retracted tissue is at risk (e.g., low oxygen saturation level, low temperature, or tissue color change).

In addition to various components described above, the controller may also contain control circuits that control operation of various sensors. For example, the control circuits may send a signal, through optical fibers or electrical wires, to an oximeter sensor or other sensors so that the sensors measure parameters associated with a retracted tissue. The timing and frequency of sensor measurements can be preprogrammed or can be input by the user.

In one embodiment, the control circuits may include signal emitter circuit and signal detector circuit. The signal emitter circuit may operate to send a signal through one or more optical fibers to the oximeter sensor. The signal detector circuit then receives a signal from the oximeter sensor via one or more optical fibers.

In some embodiments, the controller can include a first radiation source and a second radiation source. These radiation sources provide light for an oximeter sensor so that light can be transmitted into a retracted tissue and an attenuated version of the light can be received by a detector. In other embodiments, radiation sources can be located elsewhere, such as in a handle of the retractor, or in a separate enclosure.

In one implementation of the invention, a controller is a large, nonportable device that is attached to a wall or secured to a stand or surface. In this implementation, the controller is typically connected to AC power. A battery may be used to back up AC power. In another implementation of the invention, a controller is a personal computer. In another implementation of the invention, a controller is a portable console that can be hand-carried by a user. A portable console can follow a patient and measurements of tissue parameters can be made anywhere in the hospital.

Figure 2A:
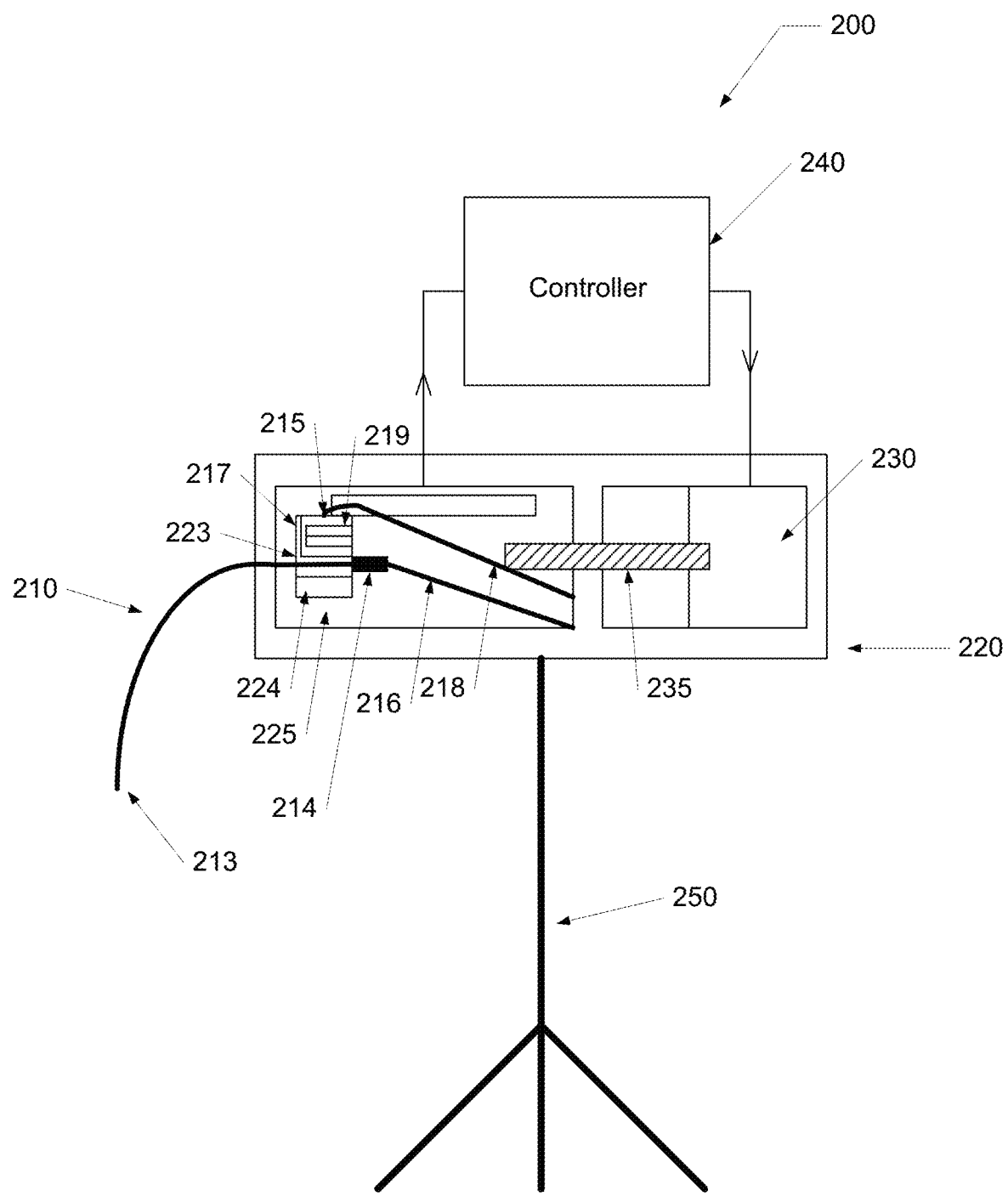
FIG. 2A shows a specific implementation of the system of FIG. 1.

FIG. 2A illustrates a more detailed view of an embodiment of a retractor system. A retractor system 200 includes a retractor 210 which is used to retract a tissue, such as a nerve. Retractor 210 includes an oximeter sensor 213 at its tip. Retractor system 200 also includes a positioning mechanism 220, which includes multiple components, to control position and movement of the retractor. A force sensor 215 (e.g., a load cell) can also be included in the system to measure an amount of force that is applied to the tissue by a tip of the retractor. System 200 further includes a controller 240 which is connected to the positioning mechanism and the sensors.

Both oximeter sensor and force sensor are functionally connected to controller 240. A proximal end of retractor 210 includes a connector 214 which connects the retractor to a cable 216. Cable 216 contains fiber optic cables or electrical wires that functionally connect oximeter sensor 213 to controller 240. Force sensor 215 has a cable 218 which transmits an electrical signal measured by the force sensor to controller 240, which is representative of the force measured.

In various implementations, controller 240 receives input signals from oximeter sensor 213 or force sensor 215, or both. Based on the input signals from the sensors (one or both sensors), the controller produces a control signal which controls movement of the positioning mechanism 220. In turn, the positioning mechanism adjusts a position of the retractor. Although this embodiment shows two sensors, in other embodiments, there may be only one sensor, or more than two sensors, and these can be used to control the positioning mechanism.

As shown in FIG. 2A, positioning mechanism 220 includes a microactuation component and a macroactuation component. The microactuation component includes a linkage element 225 and a motor 230 connected together by a gearing screw 235. Motor 230 can be a rotary driver where its rotation makes the gearing screw to rotate. The screw has a continuous helical thread around its circumference running along the length. Since linkage element 225 is connected to a gearing screw, the rotation of the gearing screw can be converted into usable linear displacement of the linkage element. Retractor 210 can be attached to the linkage element so a position of the retractor can be adjusted to retract a tissue according to movement of the motor.

The macroactuation component of positioning mechanism 220 includes a platform with a height adjustable supporting post 250. This component of the positioning mechanism can be used support the microactuation component (i.e., the linkage element and motor) so that the height of the retractor can be adjusted. By using the macroactuation component, retractor 210 can be placed in a suitable position relative to a tissue so that the retractor is ready to retract the tissue. If desired, however, the stand with a height adjustable supporting post 250 can be omitted and the retractor system can be handheld, or placed on a table or other platform.

In one implementation of the invention, retractor 210 is directly attached to linkage element 225. Retractor 210 has a shaft that is curved in the middle, with a distal end having a tip to retract a tissue. A proximal end of the shaft has a handle which can be connected to linkage element 225. In this implementation, based on oxygen saturation of a tissue measured by oximeter sensor 213 at the tip of the retractor, the controller sends a control signal to actuate the linkage element, which in turn adjusts a position of the retractor.

In another implementation of the invention, retractor 210 is indirectly attached to linkage element 225 via force sensor 215. Force sensor 215 can be a strain gauge load cell that has a first end 217 and a second end 219 along its axis. First end 217 of the force sensor is attached to retractor 210 by clamp elements 223 and 224. Second end 219 of the force sensor is attached to linkage element 225.

When linkage element 225 is pulled by motor 230, and retractor 210 moves in accordance with movement of the motor since it is connected to the linkage element via force sensor 215. When a tissue is being pulled aside by the retractor tip by movement of the linkage element, there is a force or load acting on force sensor 215 along the horizontal axis of the load cell. The load or force measured by force sensor 215 is converted into an electrical signal which is transmitted to controller 240. The electrical signal is representative of an amount of force that is applied to the tissue by the retractor tip. In this implementation, the controller can adjust movement of the retractor based on oxygen saturation measurements, force measurements, or both.

In embodiments of the invention, controller 240 receives several feedback or input signals from one or more sensors. For example, the controller receives information on oxygen saturation level of the retracted tissue from the oximeter sensor. The controller also receives information on how much force is applied to the retractor which is measured by the force sensor. The controller also receives information on a magnitude and direction of movement of the motor (and thus a retraction distance).

The controller may also receive input from the user. For example, the user may provide input through input interface information on desired oxygen saturation values or range, threshold force values, patient information, and others.

The controller processes various input signals and user input to generate a control signal that controls movement of the motor. The input signals to and the control signals from the controller can be communicated by wired connections or by any suitable wireless communications.

Figure 2B:
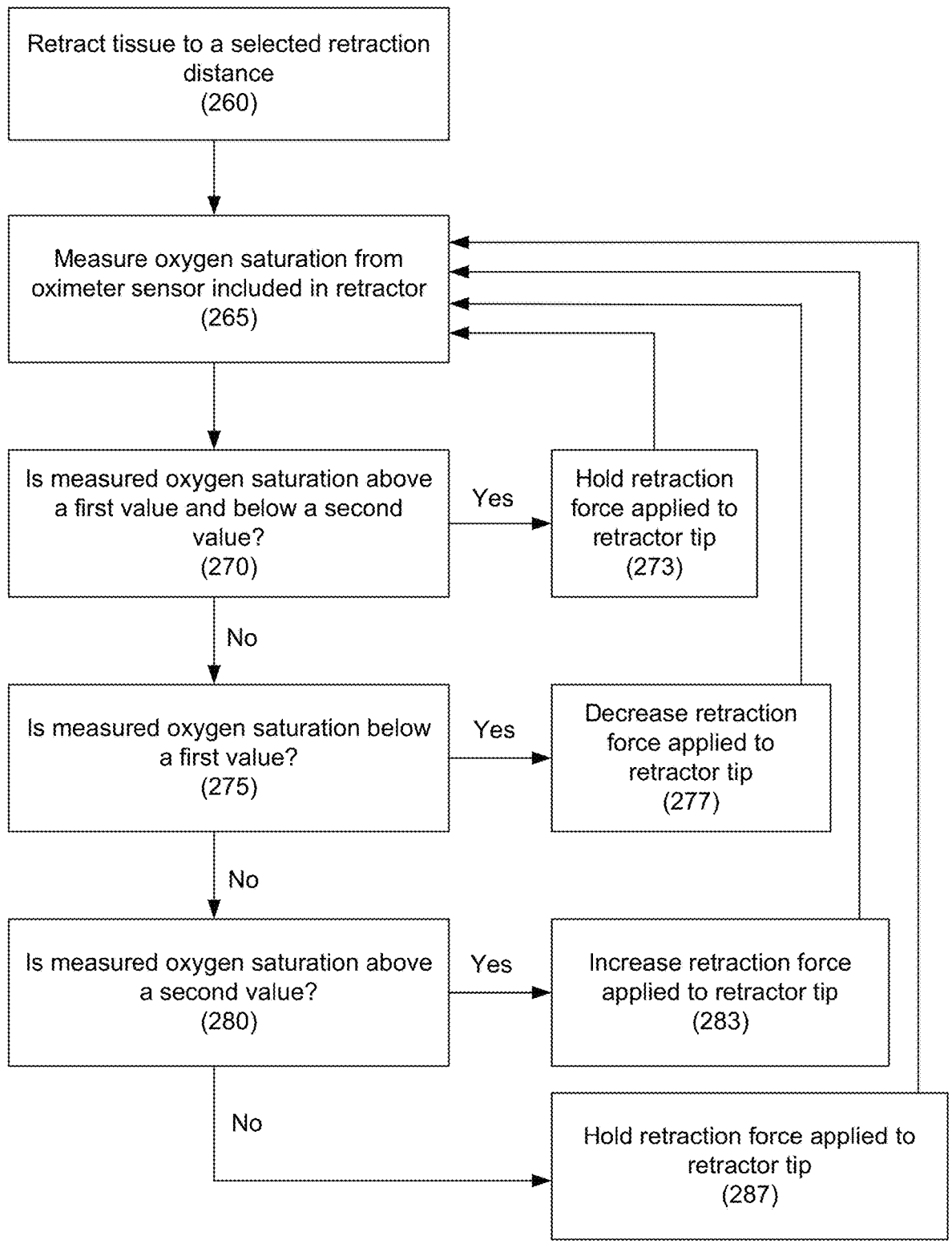
FIG. 2B shows a flow diagram for a method of using a retraction system to measure an oxygen saturation value of a retracted tissue and modifying a retraction force applied to a retractor according to the measured oxygen saturation value of the retracted tissue.

FIG. 2B shows a flow diagram that illustrates a retractor system having a closed loop control arrangement that can modulate a retraction force applied to a tip of a retractor based on a parameter of a retracted tissue measured by a sensor. Any suitable sensor can be used. As discussed, an oximeter sensor is described merely as an example below; the sensor may be any type of sensor such as a force sensor or another sensor described above.

In a step 260, a tissue is retracted to a selected retraction distance by a retractor to expose the surgical site so that the surgeon can gain access to the surgical site.

In a step 265, an oximeter sensor included in the retractor measures an oxygen saturation value of the retracted tissue and transmits this information to a controller.

In a step 270, the controller compares the measured oxygen saturation value of the retracted tissue with a first value and a second value, which are lower and upper threshold values of oxygen saturation, respectively. The first and second values may have system defaults (such as set by the factory) or may be user defined (such as being input by the user in a screen of a console). The values may be default values that can be altered by the user.

If the measured oxygen saturation value of the tissue is above the first value and below the second value (or equal to either values), then the retractor system maintains or holds a retraction force applied to the retractor tip (step 273).

In a step 275, if the controller determines that the measured oxygen saturation value of the tissue is below the first value, then the retractor system decreases a retraction force applied to the retractor tip (step 277) to reduce stress on the retracted tissue. Consequently, a retraction distance of the tissue (i.e., a linear distance that the tissue is moved from its original position by the retractor tip at the point of contact) reduces also.

In step 280, if the controller determines that the measured oxygen saturation value of the tissue is above the second value, then the retractor system increases a retraction force applied to the retractor tip (step 283). Consequently, a retraction distance of the tissue increases also.

In step 280, if the controller determines that the measured oxygen saturation value of the tissue is below a second value (but above the first value), then the retractor system maintains or holds a retractor force applied to the retractor tip (step 287).

As previously discussed, there may be multiple similar steps to steps 270-280 for each additional sensor that is used to help position the retractor. There can be any number of such sensors, one, two, three, four, five, or more.

After steps 270, 275, or 280, the system loops back to step 265 to measure an oxygen saturation value of the retracted tissue. By continuously cycling through these steps, an oxygen saturation value of the retracted tissue is constantly monitored and a retraction distance of the tissue is adjusted accordingly so that oxygen saturation level of the retracted tissue can be maintained within a predetermined range, between the first value and the second value.

The user can input and set the first and second values of oxygen saturation at any suitable level, anywhere between 0 to 100 percent. Typically, the first value (a lower limit) is set at 20, 30, 40, or 50 percent, and the second value (an upper limit) is set at 40, 50, 60, 70, or 80 percent. The second value will be set greater than the first value.

The first and second values of oxygen saturation can be set differently by the user depending on many factors. These include tissue type, general health of a patient, duration of surgery, and others. For an example, some tissues can tolerate a lower level of oxygen saturation during surgery without resulting in tissue damage, where other tissues may be more sensitive and require a higher level of oxygen saturation.

Furthermore, oxygen saturation requirements for a tissue may change during surgery and can be set differently at different time point. For example, a nerve tissue may be able to withstand a lower oxygen saturation level during the first thirty minutes of surgery, but requires a higher oxygen saturation level in the latter part of the surgery. In such a circumstance, a threshold for oxygen saturation requirements can be set lower during the first part of a surgery, and it can be reset for the latter part of the surgery to avoid any permanent damage to the tissue.

Further, the flow in FIG. 2B may also take into account an amount of time (e.g., an elapse time) that the tissue has been retracted. For example, if the tissue has been retracted (such as a sensor output being in a certain range) for more than X seconds (which may be referred to as retraction time). Then the retractor can reduce the retraction force to give the tissue Y seconds (which may be referred to as recovery time) to recover (e.g., allow full blood flow to a nerve). After recovery, then the retractor can again apply the previously applied force to the tissue.

The value of X or Y, or both, can be set by the system or there may be a default value. X may be different from Y. Some sample values for X and Y are 5 seconds, 30 seconds, 60 seconds, 120 seconds, 360 seconds, 5 minutes, 15 minutes, 30 minutes, or 60 minutes. For example, in one implementation, X is 5 minutes and Y is 30 seconds.

The elapsed retraction time may be shown on the console, so the doctor can monitor during a procedure. The display may also show a countdown to when a retractor enters into recovery mode, so the doctor can know how long he has before he has to move his instruments away. By also monitoring retraction time in addition to oxygen saturation, force applied, and other sensor outputs, damage to tissue can be minimized.

Still further, the flow in FIG. 2B may take into account of a view from visual sensor, such as a camera, attached to a retractor system. A camera can be used to determine, for example, whether there is a lack of motion or inactivity by a surgical team within its visual field at the surgical site. When there is inactivity for more than X seconds or minutes, then the retractor system can reduce the retraction force to give the tissue time to recover until the camera detects motion within its visual field. After detecting motion, then the retractor system can again apply the previously applied force to the tissue.

In another example, a camera can be used as a visual sensor to determine if an amount of pooled blood surrounding a retracted tissue exceeds a threshold value. Pooled blood surrounding a retracted tissue can interfere with accuracy of sensor measurements. For example, pooled blood may artificially increase oxygen saturation measurements of a retracted tissue measured from an oximeter sensor. When a camera detects an amount of pooled blood exceeding a threshold value, oxygen saturation measurements from an oximeter sensor can be ignored. Alternatively, suction can be applied to remove pooled blood. This can be achieved by using a retractor having an additional suction function or a separate suction tool.

A camera can also provide an instant visual verification to the doctor whether or not a retracted tissue is healthy. A retracted tissue may fade or change color if it is under stress. Moreover, a camera can also alert the doctor if a retracted tissue is about to twitch or slip away from the retractor.

In another aspect of the invention, a retractor device and system having one or more sensors can be used without a closed loop control arrangement (i.e., without a positioning mechanism). In some surgical procedures, the surgeon may wish to hold a retractor device by hand and handle it manually, rather than having it automatically controlled by a positioning mechanism. Even without the use of a positioning mechanism, sensor measurements from the retractor system can guide the surgeon to manipulate a retractor device in a manner that can preserve the health of a retracted tissue during surgery.

FIGS. 3A-3D illustrate retractor devices which can be used either manually or with a positioning mechanism in a closed loop control arrangement.

Figure 3A:
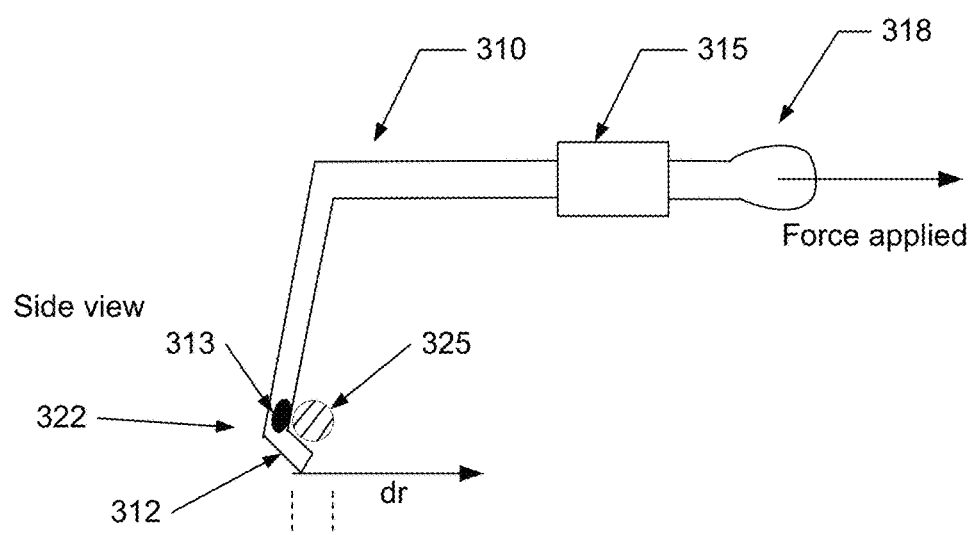
FIG. 3A shows a side view of a retractor device and a direction of force applied.

FIG. 3A illustrates a side view of a retractor device in accordance with one embodiment of the invention. The retractor device has a force sensor 315 that is connected between a retractor 310 and a handle 318. Force sensor 315 measures an amount of force applied to a tissue 325 (e.g., a nerve) by a retractor tip 322 when handle 318 is pulled to the right to retract the tissue. A retractor portion 312 cradles tissue 325 so that the tissue is ready to be pulled, and a sensor 313 measures a parameter of tissue 325 at the point of contact. For example, sensor 313 can be an oximeter sensor that measures an oxygen saturation value of tissue 325 at the point of contact.

Figure 3B:
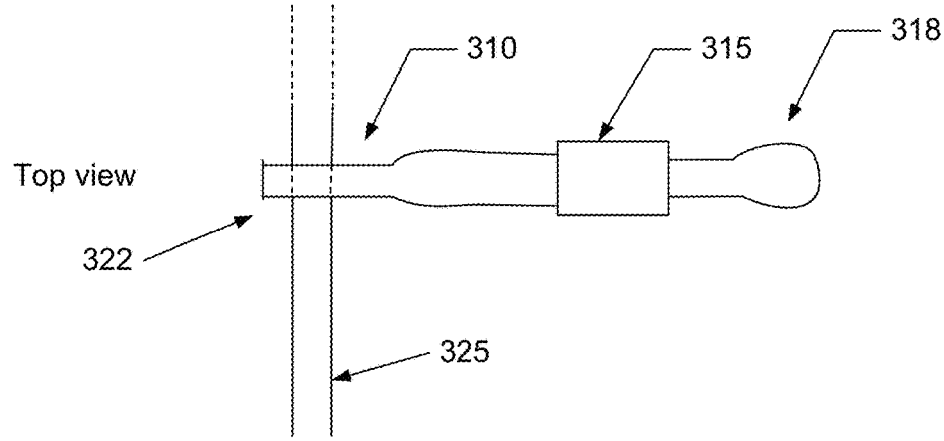
FIG. 3B shows a top view of the retractor device shown in FIG. 3A.

FIG. 3B illustrates a top view of the same retractor device shown in FIG. 3A. As shown, the retractor device includes force sensor 315 which is connected between retractor 310 and handle 318, ready to pull nerve 325 resting near tip 322 of the retractor device.

In FIGS. 3A and 3B, when the retractor device is pulled by handle 318 in a horizontal direction to the right, nerve 325 is pulled away from its original, resting position to the right. The distance that nerve 325 travels at the point of contact is referred to as a "retraction distance," shown as $d_r$ in FIG. 3A. When handle 318 pulls the retractor device in a horizontal direction to the right, then nerve 325 is pulled away from its original, resting position to the right, and a retraction distance of nerve 325 increases. When the retractor device is returned back to the left, then a retraction distance decreases to a point where the retraction distance equals zero as shown in FIGS. 3A and 3B.

In one implementation, handle 318 can be held by hand, and the retractor device can be used manually without a positioning mechanism. When the surgeon pulls the handle and retracts tissue 325, force sensor 315 measures a force which is applied to nerve 325 by retractor tip 322. The surgeon can monitor the force applied as well as other measurements of tissue parameters (e.g., oxygen saturation reading). Then the surgeon can adjust a position of the retractor device, as necessary or desired, to keep a balance between a desired retraction distance and the health of the tissue.

In another implementation, handle 318 shown in FIGS. 3A and 3B can be connected to a positioning mechanism, such as a linkage element connected to an actuator. In this implementation, force sensor 315 measures a force which is applied to nerve 325 by retractor tip 322 when a linkage element pulls handle 318 in a horizontal direction.

When a controller (not shown in FIG. 3) receives an input signal from sensor 313, which is representative of a parameter of the retracted tissue, the controller can use this input signal to adjust a linear distance that a tip of a retractor travels. A magnitude of this linear distance will be proportional to the difference between the measured parameter of the retracted tissue and a desired parameter level or range.

For example, a desired or predetermined oxygen saturation range for a tissue is preprogrammed to be between about 30 to 45 percent. A measured oxygen saturation value of the tissue at time X is 50 percent, and a measured oxygen saturation value of the tissue at time Y is 80 percent. The controller determines a difference between the measured oxygen saturation value and the desired oxygen saturation range. Since this difference is greater at time Y compared to at time X, then the controller will adjust a control signal so that a linear distance that a retractor tip travels will be greater at time Y compared to a linear distance at time X.

The controller may also make adjustments to the positioning of the retractor in order to maintain the amount of force applied within a desired range (e.g., above a first value and below a second value). The adjustments the controller makes may be a result of measurement of one or two or more sensors.

For example, if a first sensor output is within a first desired range, and a second sensor output is not within a second desired range (which may be different from the first desired range), the controller will make positioning adjustments to bring the second sensor output in range. Similarly, if a first sensor output is not within the first desired range, and the second sensor output is within a second desired range (which may be different from the first desired range), the controller will make positioning adjustments to bring the first sensor output in range. If both the first and second sensor outputs are out of range, the controller will make positioning adjustments to bring both sensors into range.

Figure 3C:
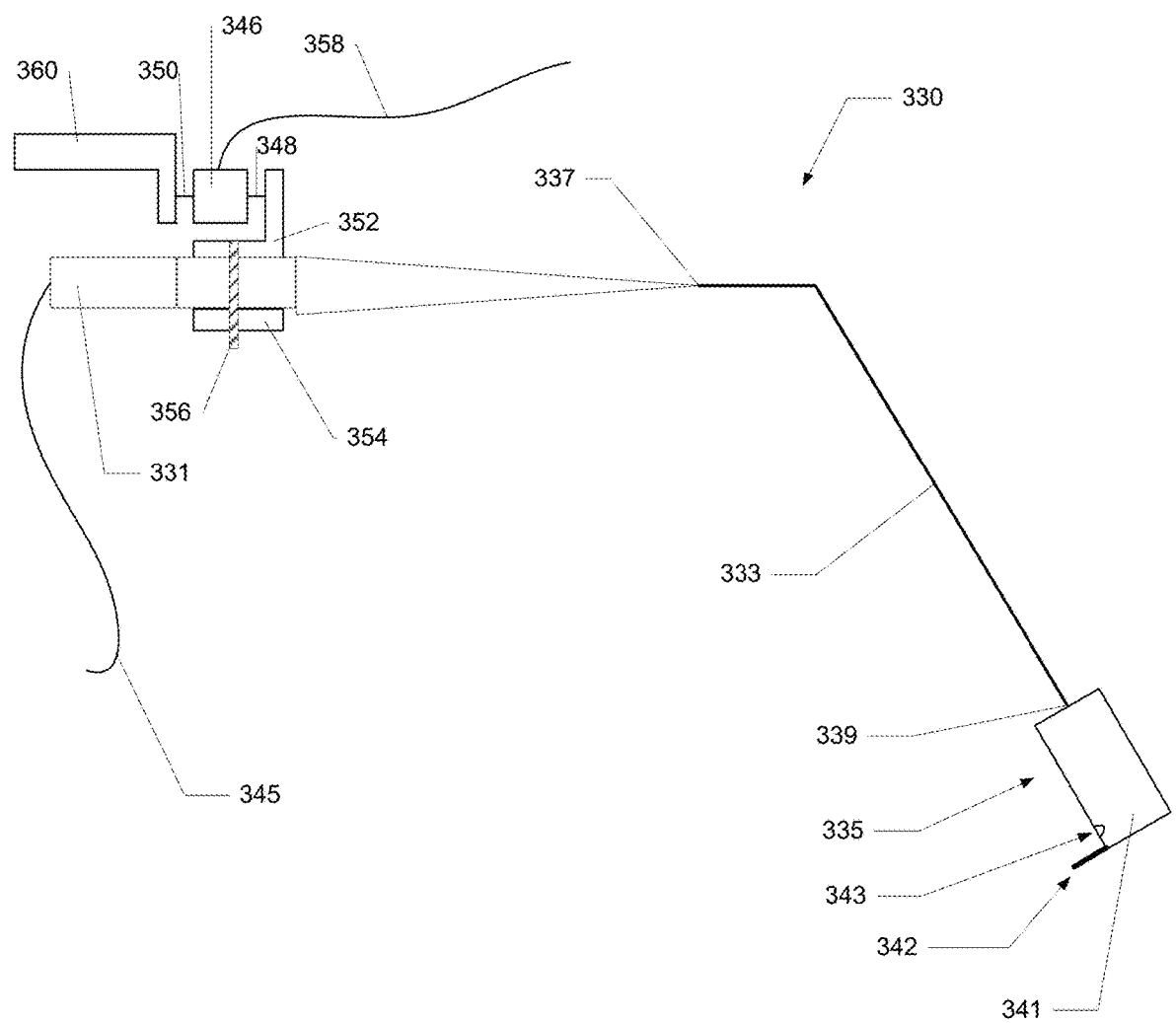
FIG. 3C shows details of a retractor device having an oximeter sensor at its tip and a force sensor near a handle.

FIG. 3C shows another retractor device 330 which can be used with or without a positioning mechanism. Retractor device 330 has a first handle 331, a shaft 333 connected at its proximal end 337 to the first handle, and a tip 335 connected to a distal end 339 of the shaft. The tip includes a retractor portion or retractor blade 342 and an oximeter sensor 343.

The shaft can include an internal channel or passageway. Optical fibers pass from sensor openings on the tip, through the channel, through the handle, and into a cable jacket or cable insulation 345. Alternatively, the optical fibers can run along the shaft and secured by, for example, shrink wrap.

Retractor device 330 also includes a force sensor 346. Force sensor 346 has a first end 348 and a second end 350 on the opposite side of the first end along the axis of force sensor s 346. Force sensor 346 measures an amount of force that is applied in a horizontal direction along its axis. First end 348 of force sensor 346 is connected to an L-shaped clamp element 352. L-shaped clamp element 352, together with a linear clamp element 354, is clamped to first handle 331 of the retractor device by a fastener 356. Second end 350 of force sensor 346 is connected to a second handle 360. Force sensor 346 also has a cable 358 (e.g., a metal wire) which transmits a signal measured by force sensor 346 to a system unit (not shown).

Retractor device 330 can be used by placing oximeter sensor 341 in contact with a tissue. Light is transmitted from a system unit or a monitoring console (not shown in FIG. 3C), through optical fiber in cable 345, out a sensor opening on tip 335 and into the tissue. The reflected light from the tissue is then received by another sensor opening on the tip, transmitted back to the monitoring console via optical fiber, and then processed. The monitoring console can display oxygen saturation measurement. The monitoring console can also display an amount of force that is applied to retract a tissue.

Retractor device 330 has two handles—first handle 331 and second handle 360. When first handle 331 is used to retract a tissue, there is no change in load or force for load cell 346 as it is not being pulled upon. When the tissue is retracted using first handle 331, oxygen saturation measurements of a retracted tissue can be made. However, a force applied to a retracted tissue will not be measured.

When second handle 360 is used to retract a tissue, since the handle is connected to load cell 346, a strain gauge in load cell 346 becomes deformed as the surgeon pulls second handle 360 to retract a tissue. The load or force measured by load cell 346 is converted into an electrical signal which is transmitted to a system unit (not shown) via cable 345. When the tissue is retracted using second handle 360, both oxygen saturation and force measurements can be made.

While FIG. 3C illustrates an embodiment of the invention where the force sensor is attached to a retractor as a separate unit and is pulled upon by a second handle, the force sensor can be an integral part of the retractor itself. For example, the force sensor can be located between first handle 331 and proximal end 337 of the shaft of the retractor. In another example, the force sensor can be located in the middle of shaft 333. In yet another example, the force sensor can be located between distal end 339 of the shaft and retractor tip 335. When the force sensor is integrated as part of a retractor, second handle 360 can be omitted in the device, and first handle 331 can be used to retract or pull aside a tissue.

Further, while FIG. 3C shows the use of a load cell as a force sensor, other types of force sensors can be used at a different location of retractor device 330. For example, a piezoresistive force sensor can be attached to a surface of retractor blade 342 that will be contacting a tissue. As described above, such piezoresistive force sensor measures an amount of force that is applied from the tissue onto the force sensor.

Although the use of an oximeter sensor is described with FIG. 3C, the sensor may be any type of sensor (e.g., a thermal sensor, visual sensor, and others) described above. Further, there can be any number of such sensors included in the retractor device shown in FIG. 3C.

Figure 3D:
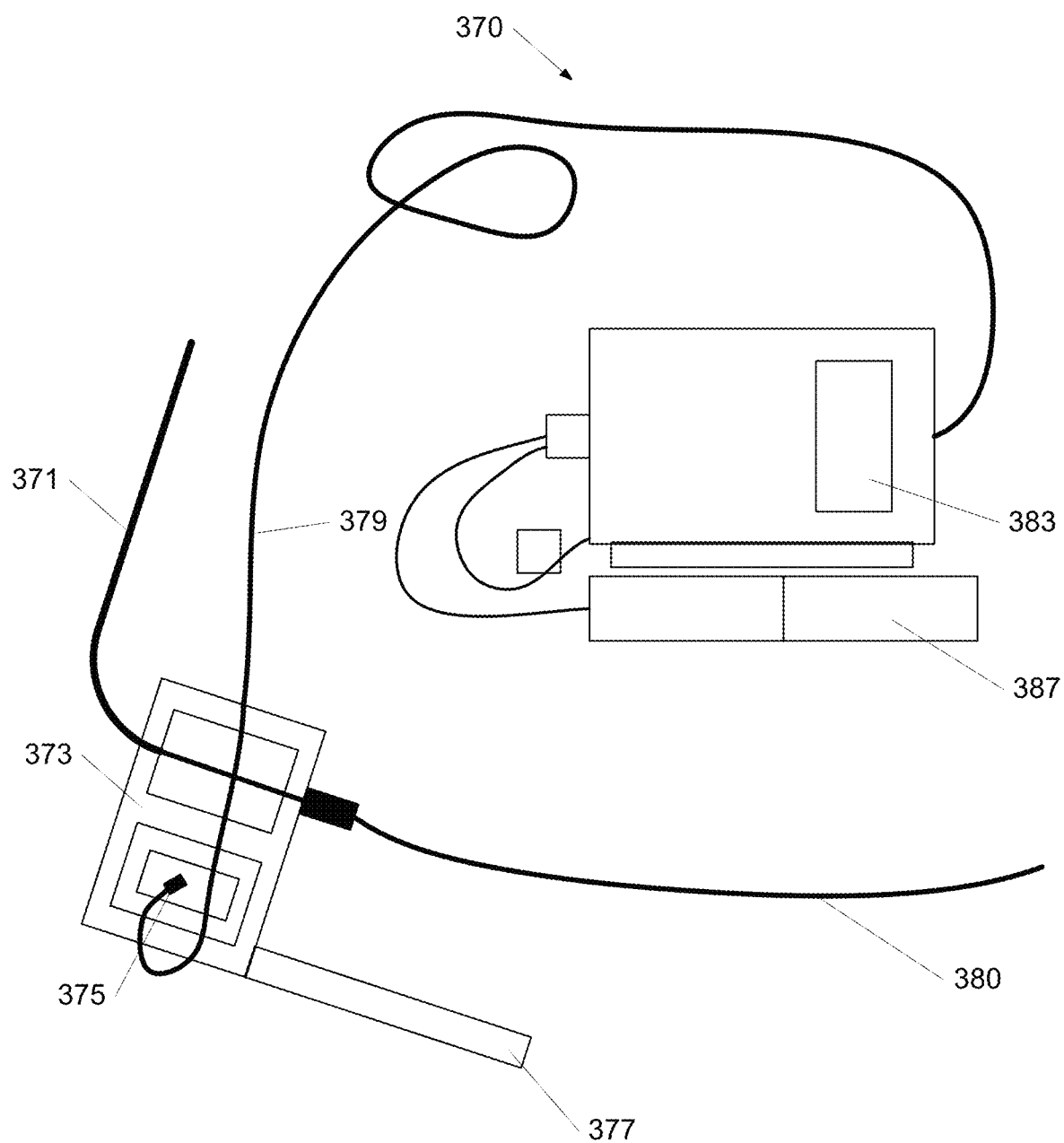
FIG. 3D shows a photograph of mechanics of a retractor system.

FIG. 3D shows a photograph of mechanics of a system 370 including a retractor device similar to that shown in FIG. 3C. System 370 includes a retractor 371 with an oximeter sensor at its tip. A handle of retractor 371 is connected to a load cell 375 by a clamp 373 at one end. The opposite end of force sensor 375 is attached to an aluminum handle 377. Load cell 375 has a cable 379 which transmits an electric signal from load cell 375 to an amplifier 385. The amplifier then amplifies the electric signal from load cell 375 and transmits the signal to a voltmeter 383 which has an LCD display. Voltmeter 383 is connected to a data recorder 387 which can store force measurements and timing of measurements.

The oximeter sensor located at the tip of retractor 371 is connected to a separate monitoring console (not shown in FIG. 3D) by a cable 380. The monitoring console can display oxygen saturation measurements of a retracted tissue or provide an audible signal. As shown in FIG. 3D, force sensor measurements and oxygen saturation measurements can be displayed by separate displays. Alternatively, they can be combined into a single console if desired.

Figure 4:
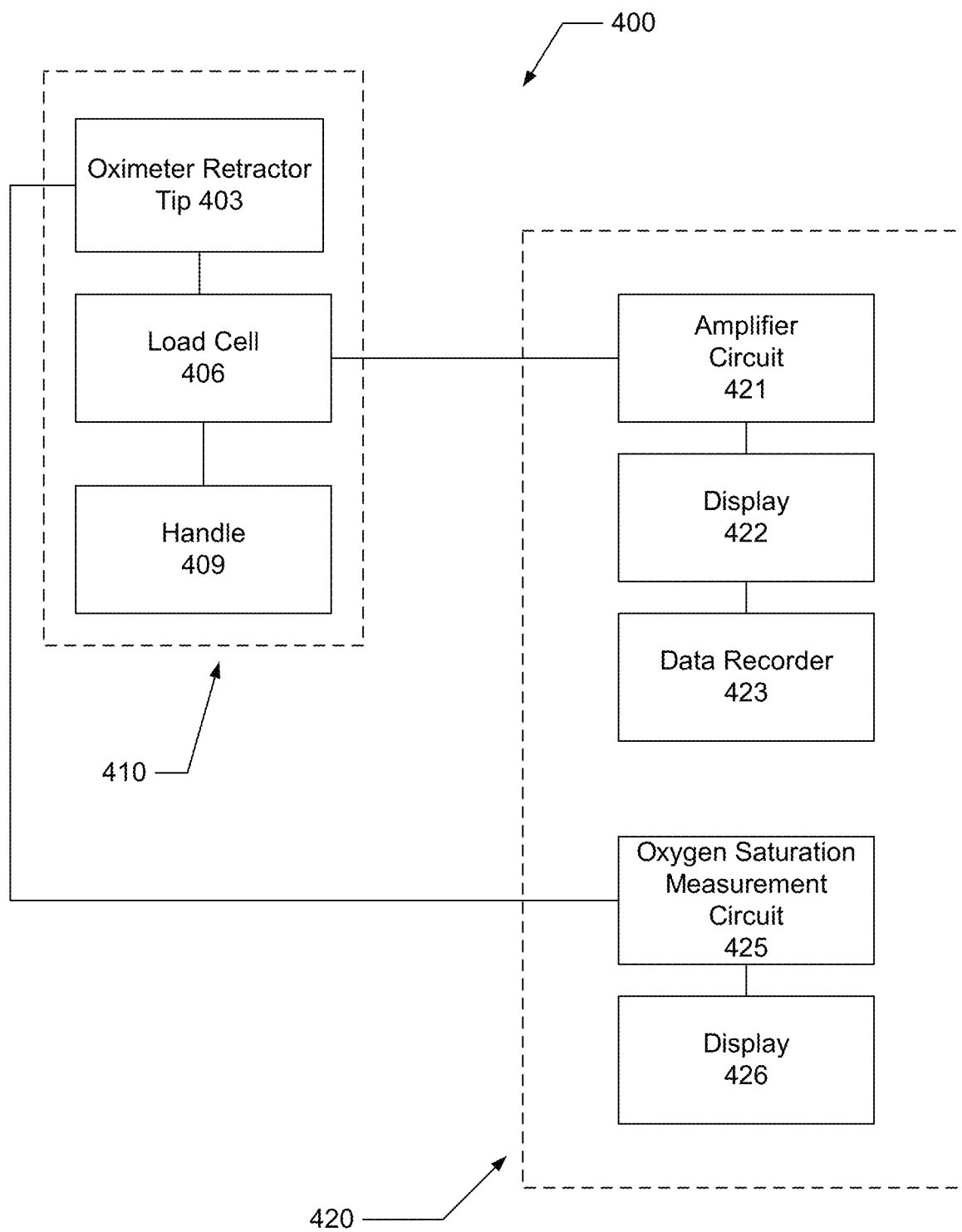
FIG. 4 shows a block diagram of a retractor system that can be used without a closed loop control arrangement.

FIG. 4 illustrates an implementation where a retractor system is used without a closed loop control arrangement. Shown in FIG. 4 is a block diagram of a system 400 that includes a retractor device 410 and a system unit 420. Retractor device 410 is used for retracting a tissue. Retractor device 410 can also be used to measure oxygen saturation of the retracted tissue and an amount of force applied to the tissue during retraction. System unit 420 can process, display, and store information provided by retractor device 410.

Retractor device 410 has an oximeter retractor tip 403 which is connected to a force sensor or load cell 406, which is in turn connected to a handle 409. Oximeter retractor tip 403 includes a retractor portion which is used to retract a tissue and an oximeter sensor which is used to measure oxygen saturation level of the tissue contacting the tip. Force sensor 406 measures an amount of force that is applied to the tissue by oximeter retractor tip 403 when a surgeon holds handle 409 and retracts or pulls aside the tissue.

System unit 420 has components that can process, display, and store information provided by retractor device 410. For example, a first set of components—an amplifier circuit 421, display 422, and data recorder 423—are functionally connected to load cell 406. A second set of components—oxygen saturation measurement circuit 425 and display 426—are functionally connected to oximeter retractor tip 403.

A signal from load cell 406 is transmitted to amplifier circuit 421, which amplifies the signal. Load cell 406 is a transducer that converts a force or load acting on it into an electrical signal. When there are changes in the force or load, there will be a change in the electrical signal. The electrical signal output from the force sensor is small, typically in the order of a few millivolts, and is amplified by amplifier circuit 421.

Display 422 (e.g., an LCD monitor or a voltmeter) can digitally display the load cell output in real time. Data recorder 423 can save the force sensor outputs and the time of measurements. For example, data recorder 423 can be a USB data logger device that can be plugged into a USB port, such as on a personal computer. Data recorder 423 can save the force sensor output once per second or at any other suitable rates, which may be selected by the user.

In the second set of components of system unit 420, oxygen saturation signals from oximeter retractor tip 403 are transmitted to oxygen saturation measurement circuit 425. Oxygen saturation measurement circuit 425 processes and analyzes the signals using algorithms and converts the signals into oxygen saturation values in terms of percentage. A display 426 is connected to oxygen saturation measurement circuit 425 to show oxygen saturation values and the timing of measurement. The oxygen saturation values, together with the time when the measurements were made, can be also stored in oxygen saturation measurement circuit 425, display 426, or other components not shown in FIG. 4.

The components of system unit 420 can be enclosed in a single housing (e.g., a console or computer). Alternatively, they can be enclosed in separate housings. For example, amplifier circuit 421 and display 422 can be enclosed in a single housing, while data recorder 423 is enclosed in a separate housing. Furthermore, some of the components shown in FIG. 4 can be combined into a single component. For example, display 422 and display 426 can be combined into a single display panel.

Figure 5:
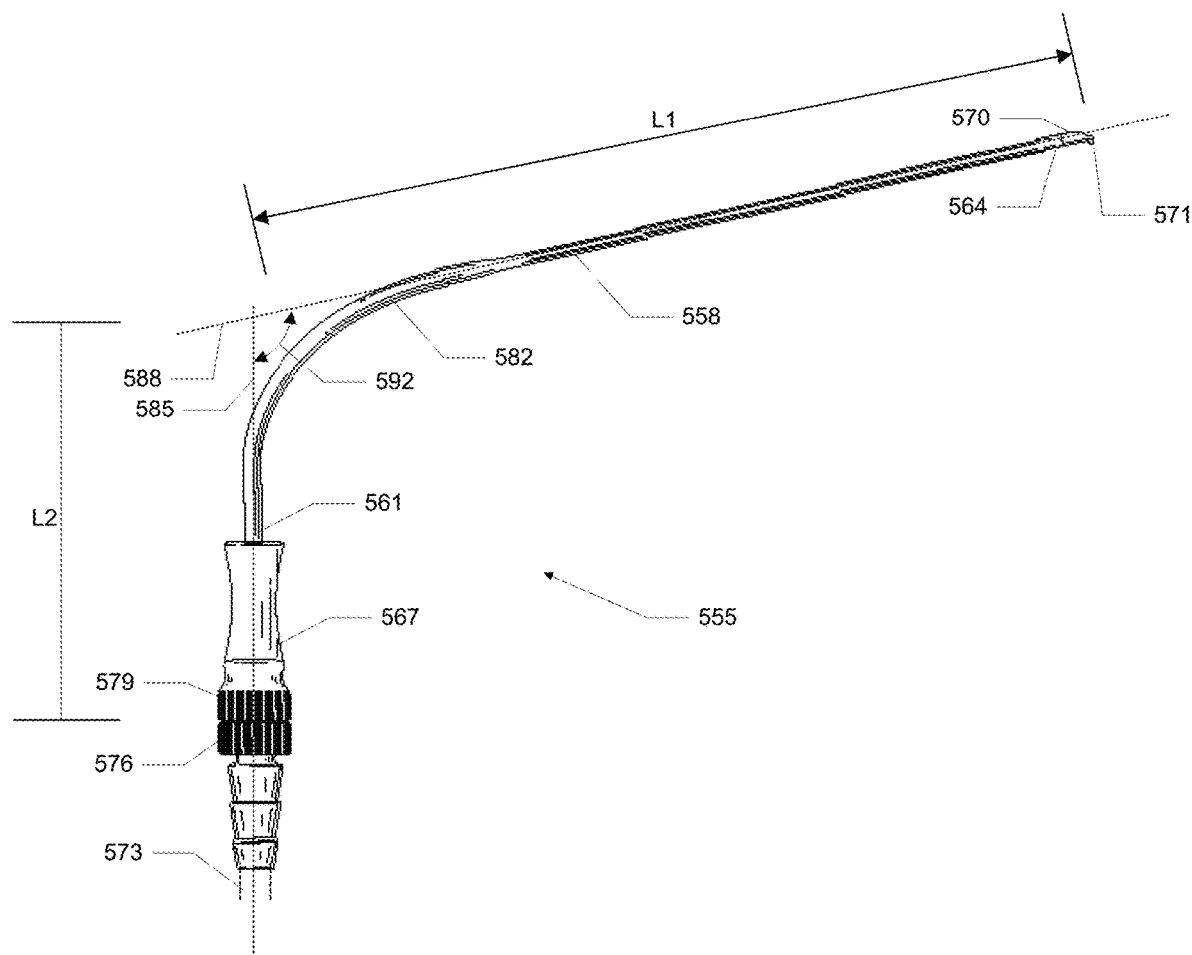
FIG. 5 shows a side view of a retractor having an oximeter sensor at its tip.

The retractor devices and systems discussed so far describe how one or more sensors can be connected to or integrated with retractor devices to provide information regarding the state of the health of a retracted tissue. In FIG. 5, shapes and materials for a nerve retractor with an oximeter sensor are described in detail. Also, FIGS. 6 through 19C describe various patterns of oximeter sensor openings at the tip of a retractor. Retractors and oximeter sensor openings described below can be combined with any other sensors (e.g., force sensor) or with a positioning mechanism described above.

While FIG. 5 provides details of a retractor for a nerve tissue, the discussions about materials and oximeter sensor opening patterns can be applied to retractors for any tissue type (e.g., liver, kidney, brain, muscle, pelvic organs, and others). The size and shape of a retractor can be adjusted based on a tissue to be retracted, and sensors can be connected to or integrated into various retractors as described in this application.

FIG. 5 illustrates a more detailed view of one embodiment of a retractor, particularly useful for a nerve tissue. A retractor 555 includes a shaft 558 with a proximal end 561 and a distal end 564. The proximal end of the shaft is connected to a handle 567. The distal end of the shaft includes a tip 570 that has a retractor portion or blade 571. Tip 570 also includes an oximeter sensor at the bottom surface of the tip near retractor portion 571.

A cable 573 may include one or more fiber optic cables or electrical wires enclosed in a flexible cable jacket. A connector 576 at one end of cable 573 is connected to a connector 579 of retractor handle 567. The other end of cable 573 (not shown) is connected to a controller, for example via another connector, so that signals can be transmitted between the controller and the oximeter sensor (or other sensors).

In one embodiment, the shaft of the retractor is hollow, including an internal channel or passageway 582 that runs the full length or some portion of the length of the shaft. The passageway may extend into the handle. The passageway can be used to contain fiber optic cables, electrical wires, or combinations of both to functionally connect an oximeter sensor or other sensors to the controller.

In another embodiment, the shaft is a solid rod, and fiber optic cables or electrical wires (electrically insulated in a cable) run along at least some portions of the length of the shaft. These cables or wires functionally connect the oximeter sensor and other sensors to a controller. In the latter embodiment, the fiber optic cables or electrical wires can be run along the shaft and secured by a jacket, for example, shrink wrap.

In yet another embodiment, fiber optic cables or electrical wires that run to the sensor openings on the bottom surface of the retractor are encased in or sealed using an epoxy, adhesive resin, plastic, or other similar material or compound. The epoxy (or other material) holds the fibers or wires in place, and prevents damage to them. The shape of the epoxy or other material may be sculpted to facilitate ease in use of the retractor.

In one implementation, the tip of the retractor has one or more openings at the bottom surface of the tip and has one or more fiber optic cables inside the openings as an oximeter sensor. The fiber optic cables at the tip of the retractor can extend through the hollow shaft of the retractor and to cable 573, which is connected to the controller. An emitter in the controller emits light which is transmitted through the fiber optic cables and out through openings in the tip of the retractor into a tissue. The fiber optic cables may also be used to transmit the light received from the tissue back to the controller.

In another implementation, an oximeter sensor may include radiation sources such as light emitting diodes (LED) and photodetectors which are placed, for example, at the tip of a retractor. In this implementation, the passageway of the retractor shaft and the cable may contain electrical wiring to transmit power to the radiation sources.

The retractor shown in FIG. 5 can be connected to a positioning mechanism in any suitable manner. For example, handle 567 can be connected to the positioning mechanism. In another example, proximal end 561 of the shaft can be connected to the positioning mechanism. A handle of the retractor makes it convenient and comfortable for the surgeon to manually hold the retractor during surgery. When a positioning mechanism is used to hold a retractor in embodiments of the invention, a handle portion of the retractor can be omitted if desired and the positioning mechanism can be attached to proximal end 561 of the retractor, or to any other suitable positions.

Although some specific dimensions, angles, and geometries, and retractor blades are shown and described in this application, one of skill in the art would understand that a retractor blade may be dimensioned or angled differently, so as to provide the appropriate control for the specific nerve or tissue being operated on. Further, the retractor may be adjustable such as having a variable length blade or a pivotable angle blade. Also, the retractor portion or blade may have different shapes, such as a hook.

Typically, the handle or the proximal end of the shaft is at an angle relative to the rest of the shaft. For example, an axis 585 passes longitudinally through the handle while an axis 588 passes longitudinally through at least a portion the shaft. The two axes form an angle 592. In a specific implementation, angle 592 is 110 degrees. However, angle 592 may be 90 degrees (i.e., a right-angle), less than 90 degrees (i.e., an acute angle), or greater than 90 degrees (i.e., an obtuse angle). Angle 592 typically ranges from about 90 degrees to about 160 degrees. This includes, for example, 95, 100, 105, 110, 115, 120, 125, 130, 135, 140, 145, 150, 155, 160, or more than 160 degrees. However, in an embodiment, the retractor has no angular difference between the handle and shaft (i.e., angle 592 is 180 degrees) and retractor is a straight puller.

The various angles allow the user to select an angle that the user is most comfortable working with. For example, one user may prefer a retractor with a 90-degree angle because the user may find that at that angle, the retractor is not sticking up towards the microscope interfering with vision and with the operating surgeon. In other implementations the shaft may be bendable by the user who can then shape the shaft into any angle or configuration. In yet another implementation, the shaft may include two or more pieces that are pivotally connected such as via screws and nuts. This too allows the user to determine and set the desired angle and configuration.

In a specific embodiment, the shaft and handle may be detached and reattached by the user. This allows, for example, the user to select an angle for the retractor and use the same handle without having to purchase a whole new retractor. The shaft may be secured to the handle using a threaded connection, a lug closure (e.g., twist and lock), a press fit, or combinations of these. In another embodiment, the shaft and the handle are secured using an adhesive or molded as a single unit.

In a specific implementation, the retractor has a shaft length L1 of about 120 millimeters and a handle length L2 of about 120 millimeters. However, these dimensions may vary widely depending on the application.

The shaft and other parts of the retractor may be made of any material suitable for use in surgery. In one embodiment, the shaft can be made of metal, such as steel, stainless steel, surgical stainless steel, gold, silver, rhodium, titanium, tungsten, aluminum, or combinations of these or other suitable materials. The shaft may be an alloy of two or more elements (e.g., iron, carbon, chromium, molybdenum, and nickel). In another embodiment, the shaft can be made of plastics, ceramics, or composites (e.g., carbon fiber). The shaft may also include a combination of materials such as steel surrounded by shrink-wrap tubing.

In an implementation of the present invention, the material of the retractor has suitable properties so that it does not interfere with surgical procedures. For example, the material of the retractor is not reflective or minimally reflected. The retractor may be coated with an antireflective material (such as a block oxide coating) to make it less reflective than the original starting material. Alternatively, the retractor may be processed (e.g., bluing, anodizing, or oxidizing), colored (e.g., black flat color), finished (e.g., matte finish), or textured (e.g., bead-blasted finish) to reduce reflectivity. Reducing reflectivity of the retractor will reduce glare for the surgeon when operating. Moreover, reducing reflectivity of the retractor will ensure that light which is transmitted into the tissue by an oximeter sensor is received back at detectors (which will be described below), instead of being reflected off the retractor.

In another implementation of the present invention, the material of the retractor is not electrically conductive or has reduced electrical conductivity compared to the original starting material. Because the retractor can be used to retract tissues including nerves, it may not be desirable to shock the nerves with electrostatic energy accidentally. The retractor may be made from material that is not conductive such as a ceramic, plastic, or resin. Alternatively, the retractor may include insulating material inserted between the tip (which touches the nerve) and the proximal end or other portions of the retractor.

In another implementation of the present invention, the material of the retractor is not thermally conductive or has reduced thermal conductivity compared to the original starting material. Because the retractor is used to retract nerves, temperature changes in the retractor can be propagated to the nerve quite quickly. It is generally desirable not to thermally heat the nerve or else it may become damaged. So, the retractor may be made from material that is not thermally conductive such as a ceramic, plastic, or resin. Alternatively, the retractor may include thermally insulating material inserted between the tip (which touches the nerve) and other portions of the retractor.

Figure 6:
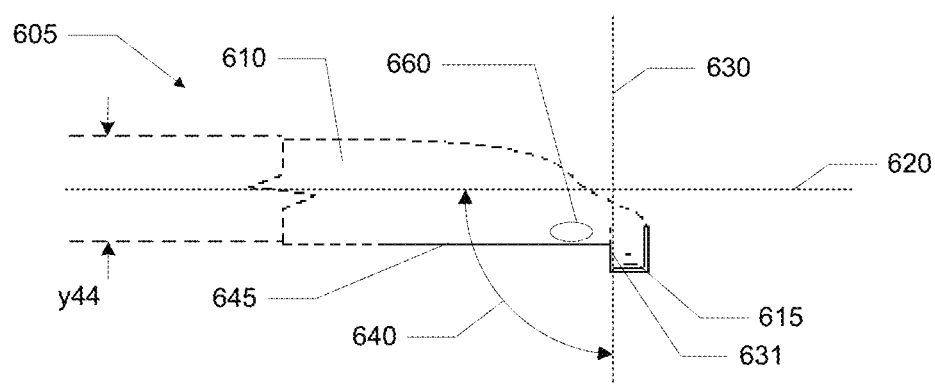
FIG. 6 shows a side view of a tip connected to the shaft of a retractor.

FIG. 6 shows a right-hand side view of a retractor tip 605. A left-hand side view of the tip is a mirror image of what is shown in FIG. 6. Tip 605 is connected to a distal end 610 of the shaft. The tip includes a retractor portion or blade 615 and a bottom surface 645. The blade is at an angle relative to the shaft and to the bottom surface. Also included at the bottom surface 645 of the tip 605 is an oximeter sensor 660. The oximeter sensor can be located at any suitable location as long as it can contact a tissue during retraction. For example, the oximeter sensor can be located at blade surface 631 or at the bottom surface 645 near the blade surface as shown in FIG. 6.

The tip has a thickness as shown by a distance of y44. In a specific implementation, the thickness is about 2 millimeters. However, the thickness may range from about 1.5 millimeters to about 5 millimeters. In some embodiments, the thickness will be less than 1.5 millimeters.

Generally, a smaller thickness (or thinner profile) is desirable to allow, for example, a smaller incision to be made. A smaller incision allows for faster healing and less scarring. Patients may also experience fewer infections.

Blade surface 631 may be flat, as shown, or angled (e.g., concave or convex) or have another contour (e.g., ogee, French curve, arch, or hook) as desired for the particular operation or intended use. The various contours on the blade surface may be part of a blade that also has one or more contours in other dimensions or planes.

For example, blade surface 631 may have a concave blade surface (from a side view as shown in FIG. 6), allowing the blade to gently cradle a portion of a round perimeter of a nerve as it is retracted. The stresses around the perimeter of the nerve may be more evenly distributed which may help prevent the nerve from traumatically creasing, folding, or compressing.

In a specific implementation, the blade surface may also have a textured surface. For example, the surface may include multiple nubs, bumps, ribs, or protrusions. These surface features may help to lift portions of the nerve away from the blade surface so as to minimize any crushing of blood vessels running alongside the nerve or to promote aeration of the nerve.

In another implementation, the blade surface may have multiple holes to promote, for example, aeration of the nerve while it is being retracted.

In yet another implementation, blade surface 631 may have a convex side (when viewed from bottom along axis 630) in addition to concave surface (when viewed from side as shown in FIG. 6). Like the concave surface, the convex side has similar benefits. That is, as the nerve is being retracted, there will be less pinching (i.e., high pressure points or relatively higher force per unit area) at the outermost points of the arc or crescent. An arc shape generally reduces the number of high stress points when retracting a nerve.

Referring now to FIG. 6, bottom surface 645 may be flat, as shown, or have another contour as desired for the particular operation or intended use. For example, the bottom surface may have a concave region to similarly cradle the nerve and distribute stress as blade surface 631. The bottom surface may also be textured (e.g., nubs, bumps, ribs, and protrusions) to lift portions of the nerve away from the bottom surface so as to minimize any crushing of blood vessels running alongside the nerve or to promote aeration of the nerve.

An axis 620 passes longitudinally through the shaft. In this specific implementation, bottom surface 645 is a flat plane that is parallel to axis 620, but this is not necessarily the case for other implementations of the retractor.

An axis 630 passes through a blade surface 631 and intersects axis 620. In this specific implementation, blade surface 631 is flat, but this is not necessarily the case for other implementations of the retractor. The blade surface is angled (i.e., angle 640) relative bottom surface 645 and axis 620.

In a specific implementation, angle 640 is about 90 degrees. However, as discussed above, the specific angle may vary. Typically, angle 640 ranges from about 90 degrees to about 179 degrees. For example, the angle may be about 100, 110, 120, 130, 135, 140, 150, 160, 170, or more than 179 degrees, such as 180 degrees. In other implementations, the angle is less than 90 degrees.

The various angles accommodate the preferences of different users and intended uses for the retractor. For example, during spinal surgery the user uses the blade to retract the nerve off to one side so that the surgeon can work on the disc without damaging the nerve. Some users may prefer to retract the nerve using a downward motion and then pulling the nerve to the side. For these users, a 90-degree blade may be appropriate.

Other users may prefer to retract the nerve using both a downward and sideways motion. For these users, a blade with an angle to the shaft greater than 90 degrees, such as 130 degrees may be more appropriate than a blade having a 90-degree angle. Further, the angle of the blade may be helpful in preventing too much force from being applied to a nerve, which may possibly damage the nerve or tissue.

Further, as shown above, the blade is angled relative to the bottom surface of the tip. But this angle is not necessarily the same angle as between the blade and the axis of the shaft. For example, in some implementations of the invention (which are not shown), the bottom surface of the tip may be perpendicular (or at another angle) relative to the axis of the shaft. Then, the blade would be angled relative to the bottom surface, but parallel to the axis of the shaft.

The blade is angled relative to the bottom surface. In a specific implementation, this angle is about 90 degrees. However, this angle may range from about 90 degrees to about 179 degrees. For example, this angle may be about 100, 110, 120, 130, 135, 140, 150, 160, 170, or more than 179 degrees, such as 180 degrees. In other implementations, the angle is less than 90 degrees.

FIGS. 7 through 10 illustrate various patterns of source structures and detector structures in an oximeter sensor located at a bottom surface at the tip of a retractor. An oximeter sensor measures oxygen saturation of a tissue. In embodiments of the invention, the oximeter sensor is located at a tip of a retractor, where it can contact and measure oxygen saturation level of a retracted portion of the tissue.

Each oximeter sensor comprises at least one source structure and at least one detector structure. A source structure is a structure in the oximeter sensor that provides light that can be transmitted into a tissue. The source structure can generate the light, or it can be a structural component that transmits the light generated elsewhere (e.g., from an upstream source). A detector structure is a structure in the oximeter sensor that detects light (or that is a structural component of the detection process) which is scattered and reflected from the tissue.

Typically, a source structure emits light (i.e., electromagnetic radiation) of one or more specific wavelengths in visible or infrared range suitable for monitoring oxygen saturation of a tissue. For example, a source structure can provide light having a wavelength from about 600 nanometers to about 900 nanometers. In one embodiment, a source structure emits light having a wavelength of 690 nanometers into a tissue, and a detector structure can receive an attenuated version of the light of the same wavelength after the light has been scattered and reflected from the tissue. In another embodiment, a source structure emits light having a wavelength of 830 nanometers, and the detector structure can receive an attenuated version of the light of the same wavelength.

In some embodiments, the source structures (e.g., radiation sources) may be dual wavelength light sources. In other words, first radiation source provides two wavelengths of radiation and second radiation source provides two wavelengths of radiation. First radiation source, second radiation source, or both may produce light in any wavelength, but typically the wavelengths range from about 600 nanometers to about 900 nanometers. In a specific implementation a first wavelength of light is generated that has a wavelength of about 690 nanometers. A second wavelength of light is generated that has a wavelength of about 830 nanometers.

In one implementation, a source structure can be a laser or light emitting diode (LED) that emits a light of a specific wavelength suitable to monitor oxygen saturation. A detector structure can be a photodiode (e.g., a PN diode, a PIN diode, an avalanche diode, and so forth) that detects the light transmitted and reflected from a tissue, after the source structure emits the light into the tissue. In an oximeter sensor, both LEDs and photodiodes are located at the scanning surface of the oximeter sensor. These LEDs and photodiodes can then be electrically connected to a system unit which will be described below. In this implementation, since the light is generated next to the tissue surface and subsequently detected at the tissue surface, there is less attenuation of a signal.

In another implementation, a source structure is an opening in an oximeter sensor (at its scanning surface) with an optical fiber inside, which is connected to a signal emitter located elsewhere (e.g., system unit). Likewise, a detector structure is an opening in an oximeter sensor (at its scanning surface) with an optical fiber inside, which is connected to a signal detector located elsewhere. The optical fibers from each oximeter sensor are then connected to either an emitter or a detector which may be located in a system unit.

Each of FIGS. 7 through 10 shows a particular opening pattern. The openings in the figures can be either source structures or detector structures, and they may be referred to herein as an opening or openings in FIGS. 7 through 10. The figures show only some examples of opening patterns, other opening patterns may be used with embodiments of the invention.

Figure 7:
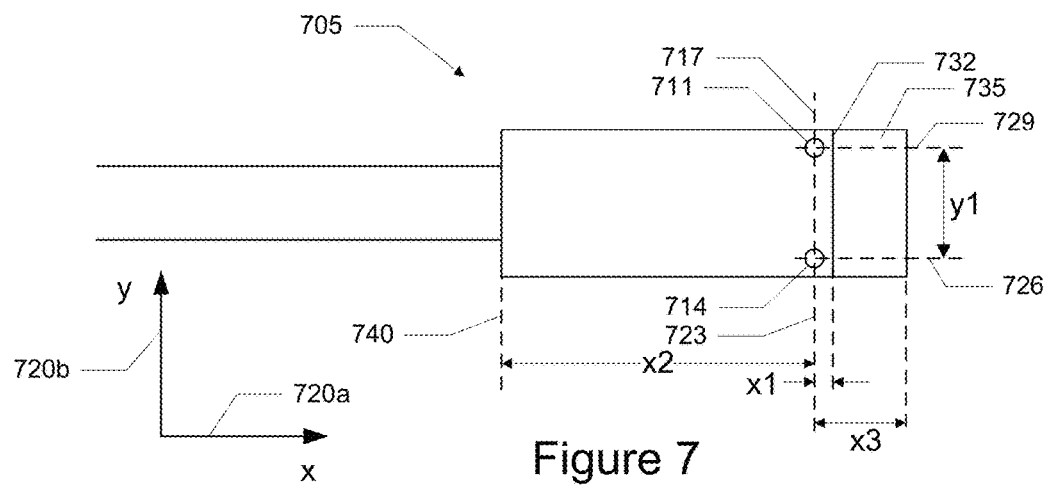
FIG. 7 shows a bottom view of a tip with a single light source and single detector symmetrical array.

FIG. 7 shows a bottom view of a tip 705 with two openings, a single light source and single detector in a symmetrical array. In the implementation shown in FIG. 7, the tip has two openings. A first opening includes a source structure 711. A second opening includes a detector structure 714.

In one embodiment, the source and detector structures generally include optical fibers that are used to measure oxygen saturation levels in tissue, such as a nerve. In an implementation, optical fiber is used having a diameter of about 1 millimeter, but other diameter fibers may be used, including 0.5 millimeter, 0.75 millimeter, 2 millimeters, 3 millimeters, 4 millimeters, 5 millimeters, and larger sizes.

The source structure typically includes an end of a first optical fiber where the opposite end of the first optical fiber is connected to a light source. The detector structure typically includes an end of a second optical fiber where the opposite end of the second optical fiber is connected to a photodetector.

In a specific implementation, the source and detector structures are in a symmetrical arrangement. For example, each source and detector structure has a reference point. The reference point may be the centers of the sources and detectors if, for example, the sources and detectors have circular shapes. Alternatively, the reference point may be defined as some other point, so long as the definition is consistent among the sources and detectors.

Lines 717 and 723 pass through the source and detector structures. Line 717 is parallel to a y-axis 720b and passes through the reference point of source structure 711. Line 723 is parallel to y-axis 720b and passes through the reference point of detector structure 714. Lines 717 and 723 are coincident. That is, source structure 711 is in a symmetrical arrangement with respect to detector structure 714.

A line 726 is parallel to an x-axis 720a and passes through the reference point of the detector structure. A line 729 is parallel to x-axis 720a and passes through the reference point of the source structure. Source structure 711 and detector structure 714 are separated by a distance y1 between lines 726 and 729.

The separation between the source and detector structures may vary widely. By way of example, distance y1 is about 1.5 millimeters. A smaller distance y1 helps to contribute to a smaller tip size. Smaller tip sizes are generally desirable because they allow the use of smaller incisions. In turn, a smaller incision allows for faster healing and less scarring. Patients may also experience fewer infections.

However, in another implementation, distance y1 is about 5 millimeters. Distance y1 generally ranges from about 1.5 millimeters to about 5 millimeters. For example, distance y1 may be about 1.5, 2, 2.5, 3, 3.5, 4, 4.5, 5, or more than 5 millimeters. In other implementations, distance y1 may be less than 1.5 millimeters.

Larger source-detector separations may allow, for example, the detector structures to detect light after the light has penetrated deeper into the tissue.

In a specific implementation where fiber optic cables are included, the size of the fiber optic cable may vary. In a specific implementation, where fiber optic cables having circular cross sections are used, the diameter of a fiber optic cable end at the source structure, detector structure, or both is approximately 0.5 millimeters, but may range from about 0.5 millimeters to about 3 millimeters. For example, the diameter may be about 0.5, 1, 1.5, 2, 2.5, 3, or more than 3 millimeters. In other implementations, the diameter of the fiber optic cable may be less than 0.5 millimeters.

Generally, the diameter of the fiber optic cable and corresponding opening will be about the same. Smaller openings allow, for example, smaller tips. Larger openings, allow, for example, more light to be transmitted into the tissue, and received from the tissue.

A distance x1 is between line 723 and an edge 732. That is, the source and detector structures may be offset by distance x1 from edge 732. Edge 732 marks the base of a retractor portion or blade 735. The source and detector structures are typically placed close to edge 732 such that distance x1 is at least about 0.5 millimeters. However, distance x1 may vary from about 0.5 millimeters to about 3 millimeters depending on the application.

Typically, the source and detector structures are located closer to the retractor portion as opposed to the distal end of the shaft. For example, a line 740 that is parallel to the y-axis passes through the distal end of the shaft.

A distance x2 is between lines 740 and 717. Generally, distance x2 will be greater than distance x1. In a specific implementation, distance x2 is about 4.8 times greater than distance x1. However, distance x2 may range from about 3 to about 6 times greater than distance x1. For example, distance x2 may be 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, or more than 5.5 times greater than distance x1. In other implementations, distance x2 may be less than 3 times greater than distance x1.

The variations of the relationship between distance x2 and distance x1 reflects the varying dimensions of a nerve or other linear tissue. For example, the diameter of a nerve may vary from patient-to-patient. It may also vary along the length of a nerve. The diameter of a nerve may range from about 1 millimeter to about 5 millimeters. For example, the nerve root in the lower back of a typical adult is about 4 millimeters in diameter. Because the nerve is typically retracted using the blade, locating the source and detector structures near edge 732 allows light to be transmitted from the source structure into the nerve and then received by the detector structure.

Generally, distance x1 will be proportional to the size of the nerve. That is, smaller nerves will result in a smaller distance x1 while larger nerves will result in a larger distance x1. Since nerves generally have circular cross-sections, this dimensional relationship helps to ensure, for example, that the source and detector structures are placed over the thickest part of the nerve, i.e., over the diameter of the nerve, when the nerve is pulled by the hook.

For example, where the nerve is small, such as the nerve of a child, the source and detector structures may be located closer to edge 732 so that the source and detector structures will be located above the nerve. Thus, light can be transmitted into the nerve and received from the nerve. Where, however, the nerve is large, such as the nerve of an adult, the source and detector structures may be located further away from edge 732.

Typically, the source and detector structures are located along one or more axes that are parallel to the longitudinal edge of the retractor portion. This allows, for example, measurements of linearly-shaped tissue such as a nerve. For example, line 717, which passes through the source and detector structures, is parallel to edge 732 of the retractor portion. During use, the nerve is typically situated against edge 732. The longitudinal axis of the nerve is then parallel to edge 732. Locating the source and detector structures along axes parallel to edge 732 helps to ensure that the nerve will be located below the source and detector structures.

A distance x3 is from line 723 to an outside edge of the blade. In a specific embodiment, distance x3 is about 1.75 millimeters. However, distance x3 may vary depending on the application including, for example, the material that the retractor is made of. For example, a material with a relatively high strength may allow for a thin blade (i.e., a shorter distance x3). However, a material with a lower strength may require a thicker blade (i.e., a longer distance x3) so that the blade is more durable, making harder to break or bend.

In a specific embodiment, the source and detector structures may be located on the blade. The source and detector structures may have similar positions, configurations, arrangements, shapes, designs, measurements, and spacings as they would have if placed on the bottom surface of the tip as discussed in this application. Furthermore, a specific embodiment may include a combination of source structures, detector structures, or both that are located on the blade and bottom surface of the tip.

One advantage of locating the source structures, detector structures, or both on the blade is that it may allow for a measurement (e.g., oxygen saturation measurement) to be made without the tissue having to contact or be positioned close to the bottom surface of the tip. For example, there may be some situations where the user is unable to fully insert the blade into the incision such that when the tissue is retracted the sensors on the bottom surface are close enough to the retracted tissue that a measurement can be made. However, sensors located on the blade may be close enough to the tissue to make the measurements.

In another implementation, the arrangement of source and detector structures is asymmetrical. An asymmetrical arrangement of source and detector structures is discussed in U.S. Pat. No. 7,355,688, which is incorporated by reference. Any of the asymmetrical arrangements of source and detector structures discussed in that patent is applicable to the sources and detectors in this application.

Figure 8:
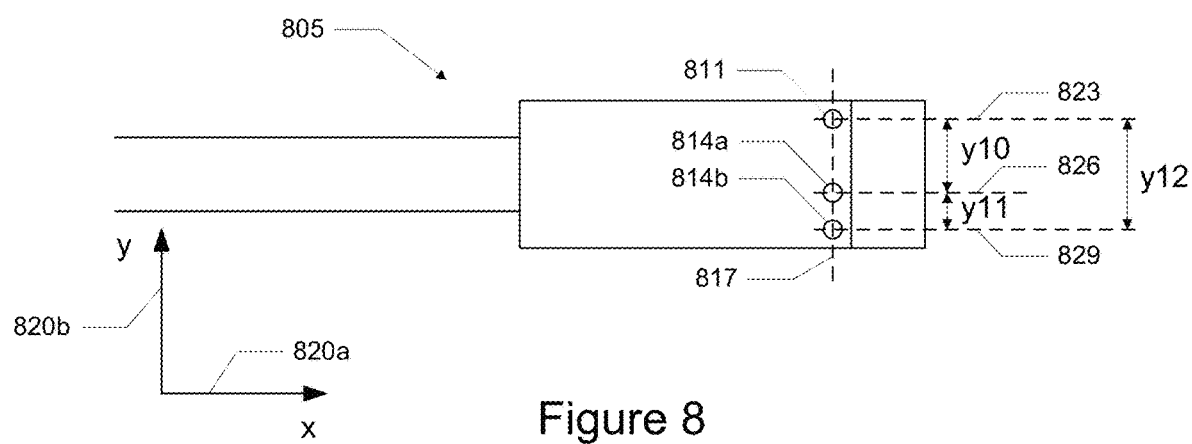
FIG. 8 shows a bottom view of a tip with a two light source and two detector symmetrical array.

For example, FIG. 8 shows a bottom view of a tip 805 with three openings, one light source and two detectors in an asymmetrical array. In the implementation shown in FIG. 8, the tip has three openings arranged on a line. A first opening includes a source structure 811. Second and third openings include detector structures 814a and 814b, respectively.

A line 817 which is parallel to a y-axis 820b passes through the reference point for each of the source and detector structures. A line 823 which is parallel to an x-axis 820a passes through the reference point of source structure 811. A line 826 which is parallel to the x-axis passes through the reference point of detector structure 814a. A line 829 which is parallel to the x-axis passes through the reference point of detector structure 814b.

The asymmetrical source and detector array of FIG. 8 includes source structure 811 and detector structure 814b, with detector structure 814a interposed between source structure 811 and detector structure 814b. Source structure 811 and detector structure 814b are located at opposite ends of the array, while detector structure 814a is located in a middle, but off-center portion of the array.

For example, a distance y10 is between lines 823 and 826. A distance y11 is between lines 826 and 829. Distance y10 is different from distance y11. Although distance y10 is shown as being greater than distance y11, it should be appreciated that distance y11 may instead be greater than distance y10. The difference between distance y10 and distance y11 is generally characteristic of the offset arrangement, or substantially unbalanced arrangement of the source structure relative to the detector structures.

A distance y12 is between lines 823 and 829. In a specific implementation, distance y11 is about one-third of the distance y12 and distance y10 is about two-thirds of the distance y12. For example, if y12 is 5 millimeters then y11 is 5/3 millimeters and y10 is 10/3 millimeters (i.e., 2/3*5 millimeters is 10/3 millimeters).

However, other implementations may include a symmetrical source-detector arrangement. For example, distance y10 may equal distance y11.

Figure 9:
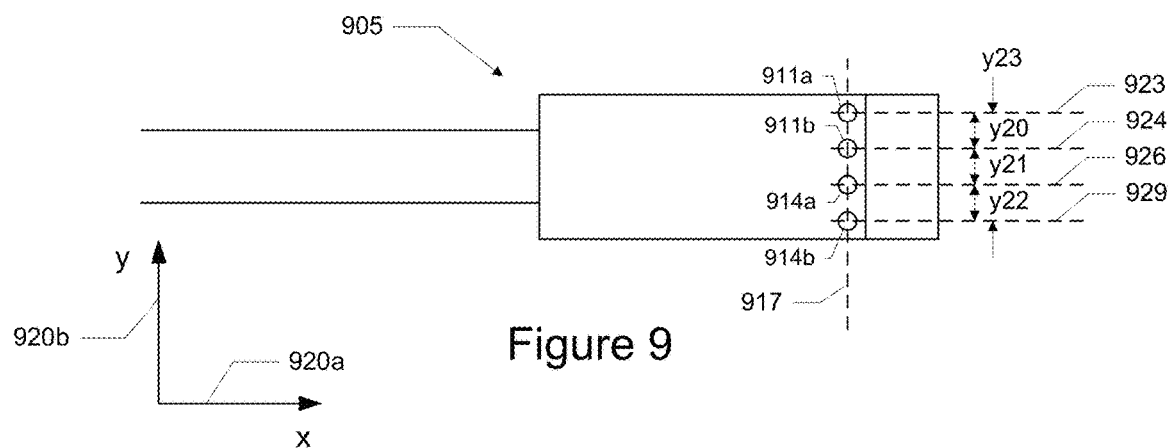
FIG. 9 shows a bottom view of a tip with a two light source and two detector symmetrical array.

FIG. 9 shows a bottom view of a tip 905 with four openings, two light sources and two detectors in a symmetrical array. In the implementation shown in FIG. 9, the tip has four openings arranged on a line. First and second openings include source structures 911a and 911b, respectively. Third and fourth openings include detector structures 914a and 914b, respectively.

A line 917 which is parallel to a y-axis 920b passes through the reference point for each of the source and detector structures. A line 923 which is parallel to an x-axis 920a passes through the reference point of source structure 911a. A line 924 which is parallel to x-axis 920a passes through the reference point of source structure 911b. A line 926 which is parallel to the x-axis passes through the reference point of detector structure 914a. A line 929 which is parallel to the x-axis passes through the reference point of detector structure 914b.

The two light source and two detector array of FIG. 9 includes source structure 911a and detector structure 914b located at opposite ends of the array, while source structure 911b and detector structure 914a are interposed between source structure 911a and detector structure 914b. That is, the arrangement shown in FIG. 9 provides the furthest separation between a source and detector structure (i.e., 911a and 914b) by locating them on opposite ends of the array. Separating source structure 911a and detector structure 914b as far as possible has advantages over other arrangements that may locate the source structures on opposite ends of the array with the detector structures interposed between. One advantage is that the light emitted from source structure 911a can travel deeper into the tissue before it is received by detector structure 914b. Another advantage is that the tip may be constructed with a very small size and therefore can be used in clinical applications where smaller instruments are advantageous because only a small incision is required to use them. Applications include, for example, spinal nerve root oxygenation measurement and monitoring in digit replantation.

In a specific implementation, the two-light-source and two-detector array is symmetrical. That is, the spacing between adjacent sources and detectors is equal. For example, a distance y20 is between lines 923 and 924. A distance y21 is between lines 924 and 926. A distance y22 is between lines 926 and 929. A distance y23 is between lines 923 and 929.

In a specific implementation, distances y20, y21, and y22 are the same. In a specific implementation, distances y20, y21, and y22 are each one-third the distance y23. For example, if y23 is 5 millimeters then y20, y21, and y22 are all 5/3 millimeters.

Figure 10:
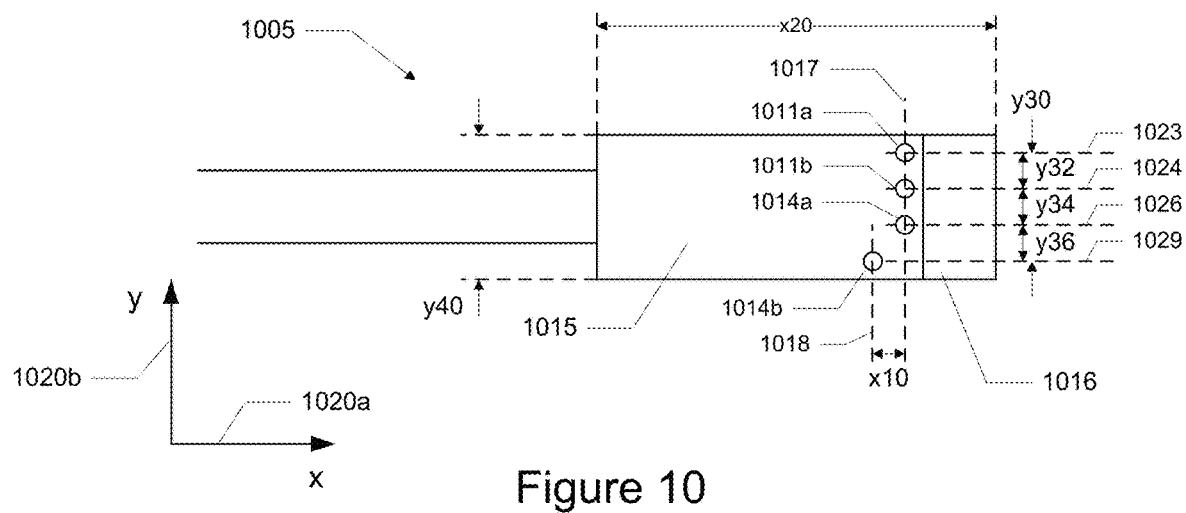
FIG. 10 shows a bottom view of a tip with a two light source and two detector asymmetrical array.

FIG. 8 described a lack of symmetry in the positioning of source and detector structures such that distances between source and detector structures varied relative to a y-axis. However, a lack of symmetry may instead or additionally have a lack of symmetry relative to an x-axis. Referring next to FIG. 10, a tip that includes a detector structure in an offset arrangement relative to a set of source structures and a detector structure will be described.

FIG. 10 shows a bottom view of a tip 1005 with four openings, where at least one of the openings is not aligned or asymmetrical with the other openings. In this figure, there is one opening that is not aligned with the openings. In another implementation, there are two openings that are not aligned with the other openings. In another implementation, there are at least three openings that are not aligned to each other. In another implementation, there are at four openings that are not aligned to each other.

A specific implementation of the figure has two light source and two detectors in an asymmetrical array. In the implementation shown in FIG. 10, the tip has four openings with three openings arranged on the same line and a fourth opening arranged offset from the line. First and second openings include source structures 1011a and 1011b, respectively. Third and fourth openings include detector structures 1014a and 1014b, respectively. The tip also includes a bottom surface 1015 and a retractor portion or blade 1016.

A line 1017 which is parallel to a y-axis 1020b passes through the reference point for source structures 1011a and 1011b and detector structure 1014a. A line 1018 which is parallel to y-axis 1020b passes through the reference point for detector structure 1014b.

A line 1023 which is parallel to an x-axis 1020a passes through the reference point of source structure 1011a. A line 1024 which is parallel to x-axis 1020a passes through the reference point of source structure 1011b. A line 1026 which is parallel to the x-axis passes through the reference point of detector structure 1014a. A line 1029 which is parallel to the x-axis passes through the reference point of detector structure 1014b.

A distance y30 is between lines 1023 and 1029. A distance y32 is between lines 1023 and 1024. A distance y34 is between lines 1024 and 1026. A distance y36 is between lines 1026 and 1029.

Lines 1017 and 1018 although parallel to the y-axis are not coincident. That is line 1017 is offset from line 1018 by a distance x10 along the x-axis, i.e., there is a lack of symmetry with respect to the x-axis. In a specific implementation x10 is about 0.5 millimeters. However, x10 may range from about 0.1 millimeters to about 2.5 millimeters. For example, x10 may be 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5 or more than 2.5 millimeters. In other implementations, x10 may be less than 0.1 millimeters.

As a further example, in an asymmetrical arrangement, the sources and detectors are arranged so there is a first distance between a first source structure (e.g., 1011a) and a first detector structure (e.g., 1014a) and a second distance between the second source structure (e.g., 1011b) and a second detector structure (e.g., 1014b), where the first and second distances are not equal.

For example, in a specific implementation, the distance along the y-axis between adjacent sensors $$\frac{n}{(m-1)},$$

is where n is the distance along the y-axis between the furthest source and detector pair and m is the number of sensors. Thus, in a specific implementation including four sensors and a y-axis distance of 5 millimeters between the furthest source and detector pair, the y-axis distance between adjacent sensors is 5/3 millimeters (i.e., $$\left(\text{i.e., } \frac{5 \text{ millimeters}}{(4-1)} = \frac{5}{3} \text{millimeters}\right).$$

In this example then, the first distance (i.e., source structure 1011a to detector structure 1014a) is 10/3 millimeters (i.e., 3.3 millimeters). The second distance (i.e., source structure 1011b to detector structure 1014b) is 3.4 millimeters, where x10 is 0.5 millimeters (i.e., second distance= $\sqrt{(0.5)^2+(3.3)^2}=3.4$).

The bottom surface is generally planar with one or more openings through which light is transmitted into the tissue and received from the tissue. However, in other implementations, the bottom surface may not be planar. For example, the bottom surface may have a convex surface, a concave surface, or both convex and concave regions.

In a specific implementation, the bottom surface may have the shape of a rectangle. However, this is not always the case. The bottom surface may have any shape. For example, in an implementation, the bottom surface may have the shape of a different type of polygon such as a square, rectangle, triangle, and parallelogram, or have a shape composed of curved line segments (e.g., oval, ellipse, and crescent), or combinations of these (e.g., semicircle).

Typically, the surface area of the bottom surface will be larger than the surface area of the openings. For example, the surface area of the bottom surface may be about two-hundred and fifty to about three-hundred and fifty times greater than the combined surface area of the openings. In other implementations, the surface area of the bottom surface will be less than or equal to the surface area of the openings.

In a specific implementation, the bottom surface has a length x20 and a width y40. In a specific implementation, such as a single source and single detector array, the bottom surface has a width of about 3 millimeters and a length of about 5 millimeters. In another implementation, such as with additional sources and detectors (e.g., two-source and two-detector array), the bottom surface may have a greater width such as 8 millimeters. Table A below shows dimensions—length x20 (FIG. 10), width y40 (FIG. 10), and thickness y44 (FIG. 6)—for various implementations of the invention, and also a range of dimensions. However, it should be noted that these dimensions may vary greatly depending upon the application.

TABLE A

| Dimension | First Implementation (millimeters) | Second Implementation (millimeters) | Third Implementation (millimeters) | Range of Dimensions (millimeters) |
|---|---|---|---|---|
| Length (x20) | 5 | 17.5 | 17.5 | 2.5-20 |
| Width (y40) | 3 | 8 | 8 | 2-20 |
| Thickness (y44) | 2 | 3 | 5 | 2-5 |

FIGS. 11 through 15 illustrate additional variations of sensor opening patterns at a bottom surface of a retractor tip, where a retractor portion at the tip has an edge profile other than a straight line.

Figure 11:
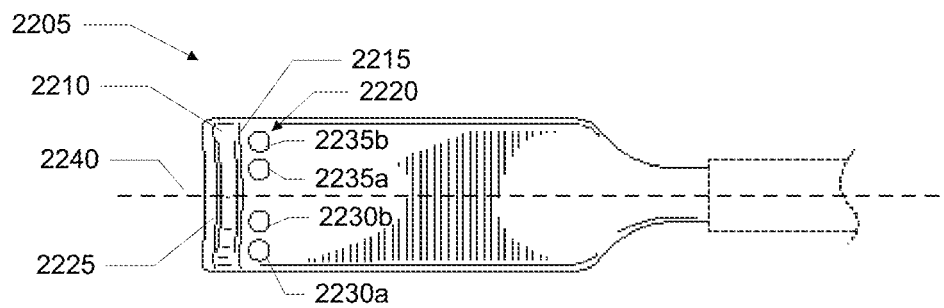
FIG. 11 shows a geometric sensor arrangement with four sensors having a spacing relative to a y-axis.

FIG. 11 shows a bottom view of an embodiment of a tip 2205. In this example, a retractor portion 2210 has an edge profile having a slight arc or crescent. A convex side 2215 of the arc is positioned near a linear source-detector array 2220. A concave side 2225 of the arc is opposite the convex side.

One advantage of the convex side of the retractor portion is a more uniform distribution of stresses across the length of the nerve as it is being retracted. That is, as the nerve is being retracted, then there will be less pinching (i.e., high pressure points or relatively higher force per unit area) at the outermost points of the arc or crescent. An arc shape generally reduces the number of high stress points when retracting a nerve. However, in other implementations, other edge profiles and shapes may be used including having the concave side of the arc positioned on the side of the source-detector array.

In the example shown in FIG. 11, the source-detector array is approximately tangent to convex side 2215. That is, the source-detector array is arranged on a line as opposed to a curve. In this embodiment, a distance from a source structure, detector structure, or both to convex side 2215 may vary. For example, a first distance from source structure 2230*a* to the convex side is different from a second distance from source structure 2230*b* to the convex side. In a specific implementation, the first distance is greater than the second distance. However, in another implementation the first distance may be less than the second distance. This may be the case, for example, when the concave side of the retractor portion is positioned on the side of the source-detector array. It may also be the case when the source structures, detector structures, or both are in an offset arrangement, i.e., not all of the source and detector structures are arranged on the same line.

Furthermore, in a symmetrical source-detector arrangement, one side (e.g., top half) is a mirror image of another side (e.g., bottom half). For example, in FIG. 11 an axis 2240 running longitudinally through the shaft divides the bottom surface into a top half and bottom half. The top half and bottom half are mirror images of each other. A third distance from detector structure 2235*a* to the convex side is equal to the second distance (i.e., source structure 2230*b* to the convex side). Likewise, a fourth distance from detector structure 2235*b* is equal to the first distance (i.e., source structure 2230*a* to the convex side).

The radius of the crescent-shaped retractor portion may be constant, as shown in FIG. 11, or it may be increasing or decreasing. For example, in a specific implementation, the radius increases from source structure 2230*a* to detector structure 2235*b*. Thus, a first distance from source structure 2230*a* to the convex side will be greater than a second distance from source structure 2230*b* to the convex side. The second distance will be greater than a third distance from detector structure 2235*a* to the convex side. The third distance will be greater than a fourth distance from detector structure 2235*b* to the convex side.

As another example, the radius may be decreasing from source structure 2230*a* to detector structure 2235*b*. Thus, a first distance from source structure 2230*a* to the convex side will be less than a second distance from source structure 2230*b* to the convex side. The second distance will be less than a third distance from detector structure 2235*a* to the convex side. The third distance will be less than a fourth distance from detector structure 2235*b* to the convex side.

In another embodiment, the source-detector array may be arranged on a curve. The curve may match the curve of the convex side of the retractor portion. Thus, a first distance from source structure 2230*a* to the convex side will equal a second distance from source structure 2230*b* to the convex side. A third distance from detector structure 2235*a* to the convex side will equal a fourth distance from detector structure 2235*b* to the convex side.

FIG. 11 also shows another example of a geometric arrangement of source structures 2230*a* and 2230*b* and detector structures 2235*a* and 2235*b*. In this first geometric arrangement, a first distance between a first source structure (i.e., 2230*a*) and a second source structure (i.e., 2230*b*) is different from a second distance between the second source structure (i.e., 2230*b*) and a first detector structure (i.e., 2235*a*). The second distance may be larger than the first distance. Furthermore, a third distance between a second detector structure (i.e., 2235*b*) and the first detector structure may be equal to the first distance.

However, many other different geometric arrangements are possible. For example, in a second geometric arrangement, the first, second, and third distances are equal. In a third geometric arrangement, the second distance is less than the first distance, third distance, or both. The first and third distances are equal. In a fourth geometric arrangement, the third distance is greater than the first distance, second distance, or both. The first and second distances are equal. In a fifth geometric arrangement, the first distance is greater than the second distance, third distance, or both. The second and third distances are equal.

FIG. 11 shows various geometric arrangements of source and detector structures relative to a single axis where the source and detector structures were all arranged on a line. However, other geometric arrangements may instead or additionally have distances between source and detector arrangements relative to a second axis.

Figure 12:
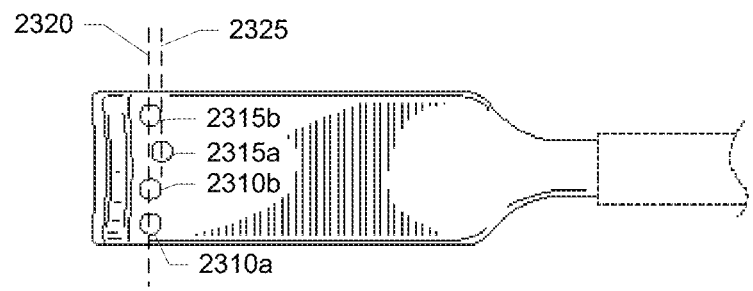
FIG. 12 shows a geometric sensor arrangement with four sensors having a spacing relative to an x-axis.

For example, FIG. 12 shows another example of a geometric arrangement having distances relative to an x-axis. This specific example includes four sensors including source structures 2310*a* and 2310*b* and detector structures 2315*a* and 2315*b*. A first distance is between a first source structure (i.e., 2310*a*) and a second source structure (i.e., 2310*b*). A second distance is between the second source structure and a first detector structure (i.e., 2315*b*). A third distance is between the first detector structure and a second detector structure (i.e., 2315*b*).

In a first geometric arrangement shown in FIG. 12, a first axis 2320 passes through the reference point of the first and second source structures and second detector structure. A second axis 2325 passes through the reference point of the first detector structure. The first axis is parallel to the second axis, but offset to the left of the second axis, i.e., the first and second axes are not coincident. In this first geometric arrangement, the third distance is equal to the second distance. The first distance is less than the third or second distance.

However, many other different geometric arrangements are possible. For example, in a second geometric arrangement, a first axis passes through the reference point of the first and second source structures and first detector structure. A second axis passes through the reference point of the second detector structure. The first axis is parallel to the second axis, but offset to the left side of the second axis, i.e., the first and second axes are not coincident. In this second geometric arrangement, the first and second distances are equal. The third distance is greater than the first or second distances.

In a third geometric arrangement, a first axis passes through the reference point of the second source structure and first and second detector structures. A second axis passes through the reference point of the first source structure. The first axis is parallel to the second axis, but offset to the left side of the second axis, i.e., the first and second axes are not coincident. In this third geometric arrangement, the first distance is greater than the second distance, third distance, or both. The second distance is equal to the third distance.

In a fourth geometric arrangement, a first axis passes through the reference point of the first and second detector structures and the first source structure. A second axis passes through the reference point of the second source structure. The first axis is parallel to the second axis, but offset to the left side of the second axis, i.e., the first and second axes are not coincident. In this fourth geometric arrangement, the third distance is less than the first distance, second distance, or both. The first distance is equal to the second distance.

In a fifth geometric arrangement, a first axis passes through the reference point of the first and second source structures. A second axis passes through the reference point of the first and second detector structures. The first axis is parallel to the second axis, but offset to the left side of the second axis, i.e., the first and second axes are not coincident. In this fifth geometric arrangement, the second distance is greater than the first distance, the third distance, or both. The first distance equals the third distance.

In a sixth geometric arrangement, a first axis passes through the reference point of the first and second detector structures. A second axis passes through the reference point of the first and second source structures. The first axis is parallel to the second axis, but offset to the left side of the second axis, i.e., the first and second axes are not coincident. In this sixth geometric arrangement, the second distance is greater than the first distance, the third distance, or both. The first distance equals the third distance.

In a seventh geometric arrangement, a first axis passes through the reference point of the second source structure and second detector structure. A second axis passes through the reference point of the first source structure and first detector structure. The first axis is parallel to the second axis, but offset to the left side of the second axis, i.e., the first and second axes are not coincident. In this seventh geometric arrangement, the first, second, and third distances are equal.

In an eighth geometric arrangement, a first axis passes through the reference point of the first source structure and first detector structure. A second axis passes through the reference point of the second source structure and second detector structure. The first axis is parallel to the second axis, but offset to the left side of the second axis, i.e., the first and second axes are not coincident. In this eighth geometric arrangement, the first, second, and third distances are equal.

In a ninth geometric arrangement, a first axis passes through the reference point of the first source structure and second detector structure. A second axis passes through the reference point of the second source structure and first detector structure. The first axis is parallel to the second axis, but offset to the left side of the second axis, i.e., the first and second axes are not coincident. In this ninth geometric arrangement, the second distance is less than the first distance, third distance, or both. The first distance is equal to the third distance.

In a tenth geometric arrangement, a first axis passes through the reference point of the second source structure and first detector structure. A second axis passes through the reference point of the first source structure and second detector structure. The first axis is parallel to the second axis, but offset to the left side of the second axis, i.e., the first and second axes are not coincident. In this tenth geometric arrangement, the second distance is less than the first distance, third distance, or both. The first distance is equal to the third distance.

Figure 13:
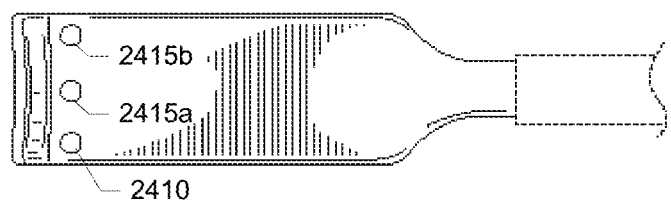
FIG. 13 shows a geometric sensor arrangement with three sensors having a spacing relative to a y-axis.

FIG. 12 shows various source and detector geometric arrangements with respect to the tip having four openings. However, similar geometric arrangements may be had for tips with more than four or less than four openings. FIG. 13 shows a source and detector geometric arrangement where the tip includes three openings. This specific example includes a source structure 2410 and detector structures 2415a and 2415b. A first distance is between the source structure and a first detector structure (i.e., 2415a). A second distance is between the first detector structure and a second detector structure (i.e., 2415b). The source and detector structures may be arranged on a line. In this first geometric arrangement, the first and second distances are equal.

However, many other different geometric arrangements are possible. For example, in a second geometric arrangement, the first distance is less than the second distance.

In a third geometric arrangement, the first distance is greater than the second distance.

FIG. 13 shows various geometric arrangements of source and detector structures relative to a single axis where the source and detector structures are arranged on the same line. However, other geometric arrangements may instead or additionally have distances between source and detector arrangements relative to a second axis.

Figure 14:
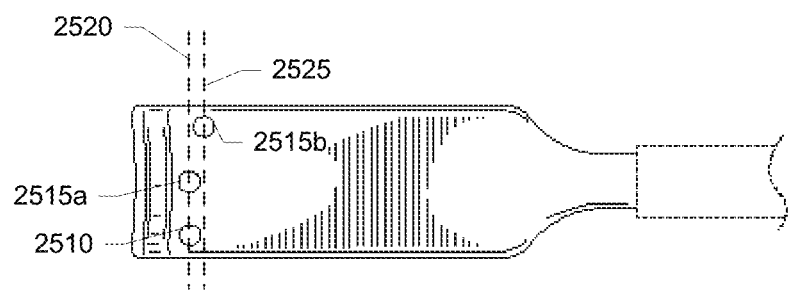
FIG. 14 shows a geometric sensor arrangement with three sensors having a spacing relative to an x-axis.

For example, FIG. 14 shows another example of a geometric arrangement having distances relative to an x-axis. This specific example includes three sensors including a source structure 2510 and detector structures 2515a and 2515b. A first distance is between the source structure and a first detector structure (i.e., 2515a). A second distance is between the first detector structure and a second detector structure (i.e., 2515b).

In a first geometric arrangement shown in FIG. 14, a first axis 2520 passes through the reference point of source structure and first detector structure. A second axis 2525 passes through the reference point of the second detector structure. The first axis is parallel to the second axis, but offset to the left side of the second axis, i.e., the first and second axes are not coincident. In this first geometric arrangement, the first distance is less than the second distance.

However, many other different geometric arrangements are possible. For example, in a second geometric arrangement, a first axis passes through the reference point of the first and second detector structures. A second axis passes through the reference point of the source structure. The first axis is parallel to the second axis, but offset to the left side of the second axis, i.e., the first and second axes are not coincident. In this second geometric arrangement, the first distance is greater than the second distance.

In a third geometric arrangement, a first axis passes through the reference point of the first source structure and second detector structure. A second axis passes through the reference point of the first detector structure. The first axis is parallel to the second axis, but offset to the left side of the second axis, i.e., the first and second axes are not coincident. In this third geometric arrangement, the first distance is equal to the second distance.

In a fourth geometric arrangement, a first axis passes through the reference point of the first detector structure. A second axis passes through the reference point of the first source structure and second detector structure. The first axis is parallel to the second axis, but offset to the left side of the second axis, i.e., the first and second axes are not coincident. In this fourth geometric arrangement, the first distance is equal to the second distance.

FIG. 14 shows various source-detector geometric arrangements with respect to the tip having three openings. However, similar geometric arrangements may be had for tips with less than three openings, such as two openings.

Figure 15:
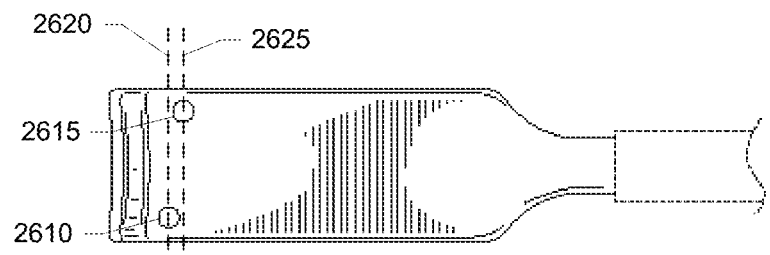
FIG. 15 shows a geometric sensor arrangement with two sensors having a spacing relative to an x-axis.

FIG. 15 shows a source and detector geometric arrangement where the tip includes two openings. This specific example includes a source structure 2610 and a detector structure 2615. A first axis 2620 passes through the reference point of the source structure. A second axis 2625 passes through the reference point of the detector structure. The first axis is parallel to the second axis, but offset to the left side of the second axis, i.e., the first and second axes are not coincident.

In another embodiment, a first axis passes instead through the reference point of the detector structure and the second axis passes through the reference point of the source structure. The first axis is parallel to the second axis, but offset to the left side of the second axis, i.e., the first and second axes are not coincident.

FIGS. 16 through 19C show additional patterns of source structures and detector structures in an oximeter sensor in asymmetric arrangements. Each figure shows a particular opening pattern, and any of these may be used in conjunction with any of the implementations discussed in this application. Contrary to FIGS. 7-15 which illustrate the entire bottom surface of a retractor tip including a retractor portion, FIGS. 16 through 19C illustrate just sensor openings. A retractor portion or blade can be located at any suitable position in embodiments shown in FIGS. 16 through 19C.

Figure 16:
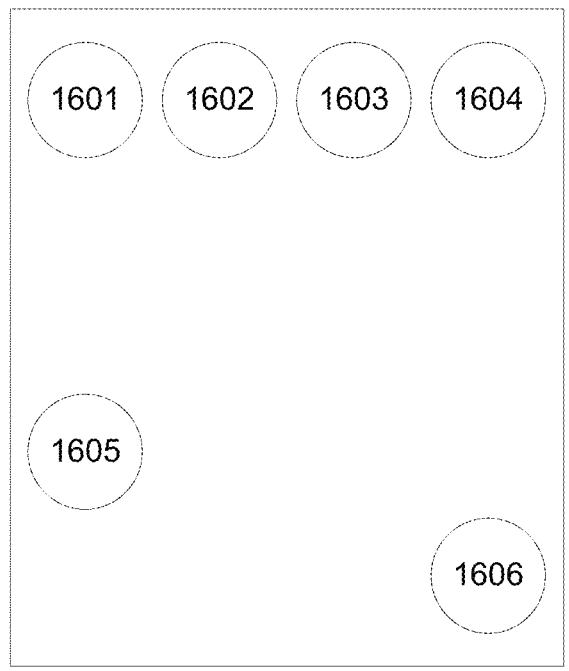
FIG. 16 shows a sensor opening pattern where one sensor opening is aligned asymmetrically with respect to the other sensor openings.

FIG. 16 shows a specific implementation of an oximeter sensor. This sensor has six openings 1601-1606. Openings 1601-1604 are arranged in a line closer to a first edge of the sensor, while openings 1605 and 1606 are arranged closer to a second edge, which is opposite the first edge. In fact, opening 1606 is closer than opening 1605 to the second edge. These openings are for sources and detectors, and there can be any number of sources, any number of detectors, and they can be in any combination. In an implementation of an oximeter sensor, the first edge is distal to the second edge, which is closer to a cable attached to the probe or hand holding the probe.

In one implementation, openings 1601-1604 are detectors while openings 1605 and 1606 are sources. However, in other implementations, there can be one or more detectors, two or more detectors, one or more sources, or two or more sources. For example, there may be three detectors and three sources or one detector and five sources.

In FIG. 16, the openings are positioned asymmetrically such that a line drawn through openings 1601-1604 is not parallel to a line drawn through openings 1605 and 1606. However, a line drawn through openings 1601 and 1605 is parallel to a line through openings 1604 and 1606. Additionally, the distance between openings 1601 and 1604 is shorter than the distance between openings 1605 and 1606.

Thus, the distance between openings 1601 and 1605 does not equal the distance between openings 1601 and 1606; the distance between openings 1602 and 1605 does not equal the distance between openings 1603 and 1605; and the distance between openings 1603 and 1605 does not equal the distance between openings 1604 and 1606.

In this implementation, the oximeter sensor has a rectangular shape, but the sensor unit may have any shape such a trapezoid, triangle, dodecagon, octagon, hexagon, square, circle, or ellipse. A sensor of any shape or form can incorporate the sensor openings in the pattern shown and described.

In a specific implementation, a distance between openings 1601 and 1604 is five millimeters. A distance between each of the openings 1601, 1602, 1603, and 1604 is 5/3 millimeters. A distance between 1601 and 1605 is five millimeters. A diameter of an opening is one millimeter.

Figure 17:
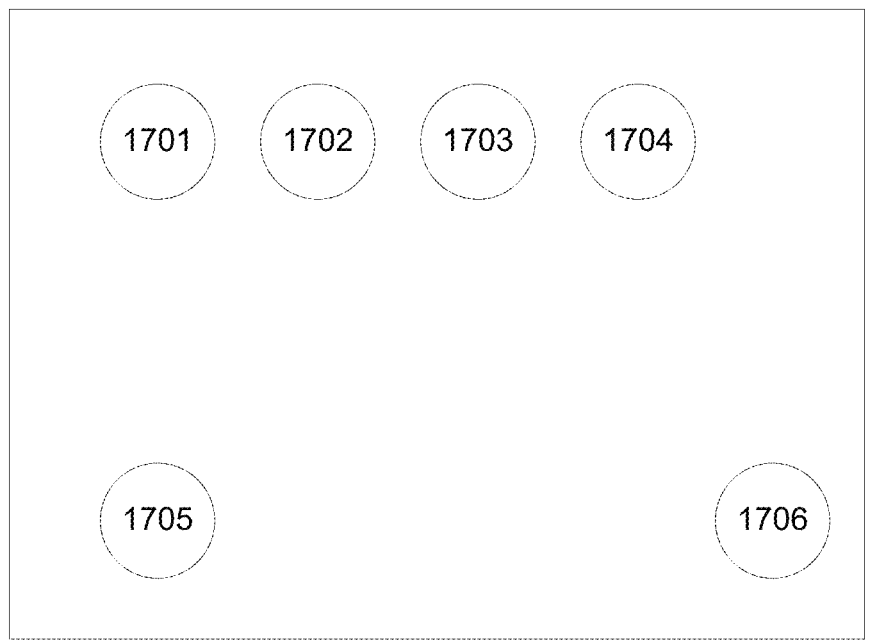
FIG. 17 shows another sensor opening pattern where one sensor opening is aligned asymmetrically with respect to the other sensor openings.

FIG. 17 shows a variation of the implementation of the oximeter sensor shown in FIG. 16. The oximeter sensor in this specific implementation is also arranged to include six openings 1701-1706. Similar to FIG. 16, openings 1701-1704 are arranged in a line closer to a first edge of the sensor, while openings 1705 and 1706 are arranged closer to a second edge, which is opposite the first edge. In one implementation, openings 1701-1704 are detectors while openings 1705 and 1706 are sources.

In this figure, the openings are positioned so that a line drawn through openings 1701-1704 is parallel to a line through openings 1705 and 1706. However, a line drawn through openings 1701 and 1705 is not parallel to a line through openings 1704 and 1706.

Additionally, similar to FIG. 16, the distance between openings 1701 and 1704 is shorter than the distance between openings 1705 and 1706. Thus, the distance between openings 1701 and 1705 does not equal the distance between openings 1701 and 1706; the distance between openings 1702 and 1705 does not equal the distance between openings 1703 and 1705; and the distance between openings 1703 and 1705 does not equal the distance between openings 1704 and 1706.

In this implementation, the oximeter sensor unit itself is of a greater area relative to the area of the oximeter sensor unit shown in FIG. 16. In another implementation, the oximeter sensor unit may be of a smaller area relative to the area shown in FIG. 16. In yet another implementation, the oximeter sensor unit may be of a greater area relative to that shown in FIG. 16.

Further, in a specific implementation, the openings are the same size as each other (e.g., each opening has the same diameter or each opening has the same area). A specific implementation uses one-millimeter circular openings. However, in another implementation, the diameter of one opening may be different from other openings, or there may be some openings with different diameters than other openings. There can be any combination of differently sized openings on one sensor unit. For example, there are two openings with a C size and other openings have a D size, where C and D are different and D is greater than C. Also, openings are not necessarily circular. So, C and D may represent area values.

Figure 18:
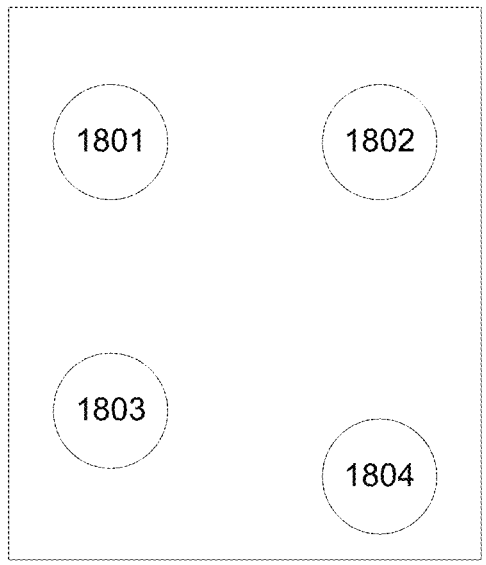
FIG. 18 shows another sensor opening pattern where one sensor opening is aligned asymmetrically with respect to the other sensor openings.

FIG. 18 shows a specific implementation of an oximeter sensor which is arranged to include four openings 1801-1804. Openings 1801 and 1802 are arranged in a line closer to a first edge of the sensor, while openings 1803 and 1804 are arranged closer to a second edge, which is opposite the first edge. In fact, opening 1804 is closer than opening 1803 to the second edge. In an implementation the first edge is distal to the second edge, which is closer to a cable attached to the probe or hand holding the probe.

In one implementation, openings 1801 and 1802 are detector structures and openings 1803 and 1804 are source structures. However, in other implementations, there can be one or more detector structures, two or more detector structures, one or more source structures, or two or more source structures. For example, there may be three detector structures and one source structure or one detector structure and three source structures.

In FIG. 18, the openings are positioned asymmetrically such that a line drawn through openings 1801 and 1802 is not parallel to a line through openings 1803 and 1804. However, a line drawn through openings 1801 and 1803 is parallel to a line through openings 1802 and 1804.

Additionally, the distance between openings 1801 and 1802 is shorter than the distance between openings 1803 and 1804. Thus, in FIG. 18, the distance between openings 1801 and 1803 does not equal the distance between openings 1802 and 1804 and the distance between openings 1802 and 1803 does not equal that between openings 1802 and 1804.

Figure 19A:
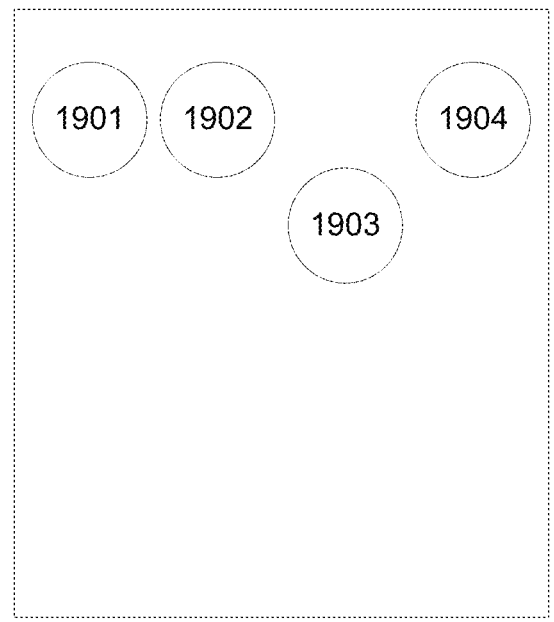
FIG. 19A shows a sensor opening pattern where the openings are aligned in a row, except for one of the openings.

FIG. 19A shows another variation of the implementation of the oximeter sensor. This implementation of an oximeter sensor is similarly arranged to include four openings 1901-1904. Also, this arrangement of openings is located closer to a first edge of the sensor. However, in this figure, openings 1901, 1902, and 1904 lie in a row parallel to the first edge so that a straight line may be drawn through the center of each opening, while opening 1903 lies below that straight line.

In this implementation, opening 1903 lies equally spaced between openings 1902 and 1904; in other implementations, opening 1903 can lie closer to one opening than another. In one implementation, openings 1901 and 1902 are detectors and openings 1903 and 1904 are sources.

In this specific implementation, as mentioned above, the distance between openings 1902 and 1903 equals that between openings 1903 and 1904. Aside from this equality, the distances between the openings are unequal. For example, in this implementation, the distance between openings 1901 and 1903 does not equal the distance between openings 1902 and 1904 and the distance between openings 1902 and 1903 does not equal that between openings 1902 and 1904.

Although oximeter sensors with two, four, and six openings are shown in these figures, other implementations may include different numbers of sensor openings. For instance, there may be three, five, seven, eight, or more openings.

Further, there may be any combination of detector structures and source structures and the number of detector structures need not equal the number of source structures. For instance, if there are three openings, there may be one detector structure and two source structures or two detector structures and one source structure. As another example, if there are eight openings, there may be two detector structures and six source structures, five detector structures and three source structures, or four detector structures and four source structures.

In another implementation of the invention, an oximeter sensor at the tip of a retractor includes only a single opening, rather than multiple openings, and a single optical fiber or single optical fiber bundle is connected to the single opening. The optical fiber or optical fiber bundle may be made of glass or plastic. In this implementation, a single optical fiber or fiber bundle is used to emit light into a tissue and to receive reflected light from the tissue from the same opening at the retractor tip.

Figure 19B:
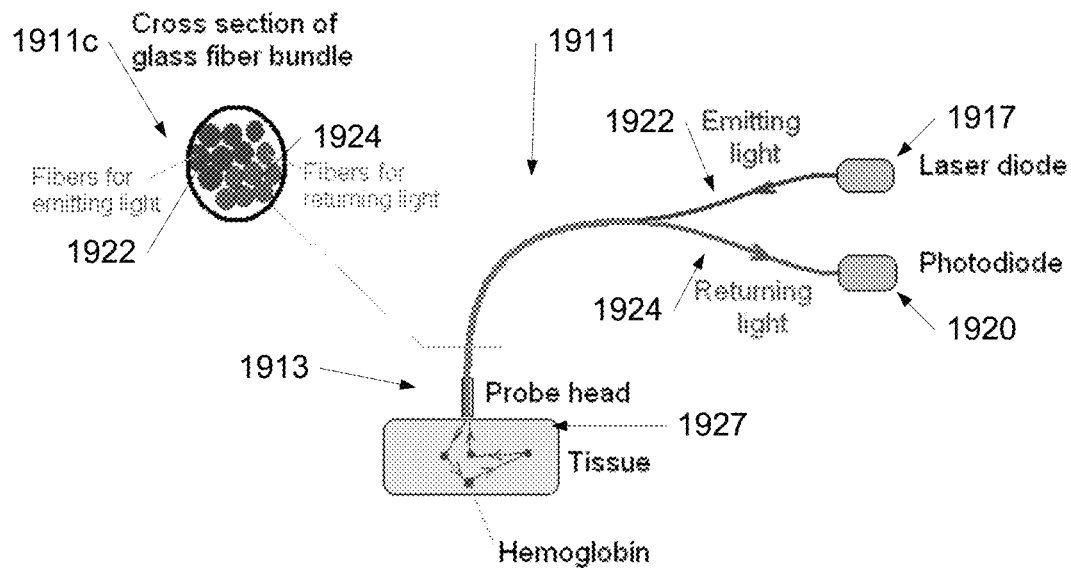
FIG. 19B shows a retractor oximeter that has a single sensor opening at the tip and a single optical fiber bundle connected to the sensor opening at a distal end.

FIG. 19B illustrates an implementation where a single glass optical fiber bundle is connected to a single opening at the tip of a retractor. Shown in FIG. 19B is a single optical fiber bundle 1911 which is connected to a single opening in the tip of a retractor (referred to as "probe head" 1913 in FIG. 19B). A cross section of a fiber bundle 1911c shows that about a half of the optical fibers in the bundle (referred to as optical fibers 1922) is used for emitting light. The other half of the optical fibers in the bundle (referred to as optical fibers 1924) is used for returning light.

As shown in FIG. 19B, optical fibers 1922 are connected to a laser diode 1917, and optical fibers 1924 are connected to a photodiode 1920. When light is emitted from laser diode 1917, optical fibers 1922 carry the light into the tissue. The light scatters in the tissue and is reflected back to optical fibers 1924 which return an attenuated version of the light to the photodiode. The emitting light and returning light travels in the same single fiber bundle, but in opposite direction.

Any suitable number of optical fibers can be contained in a single bundle. For example, an optical fiber bundle may contain two (a first fiber for emitting light and a second fiber for returning light), three, four, five, six, tens, hundreds, or more optical fibers. In an optical fiber bundle, a number of optical fibers used for emitting light may not equal to those used for returning light. For example, if the bundle has five optical fibers, two optical fibers may be used for emitting light and three optical fibers may be used for returning light, or vice versa.

Figure 19C:
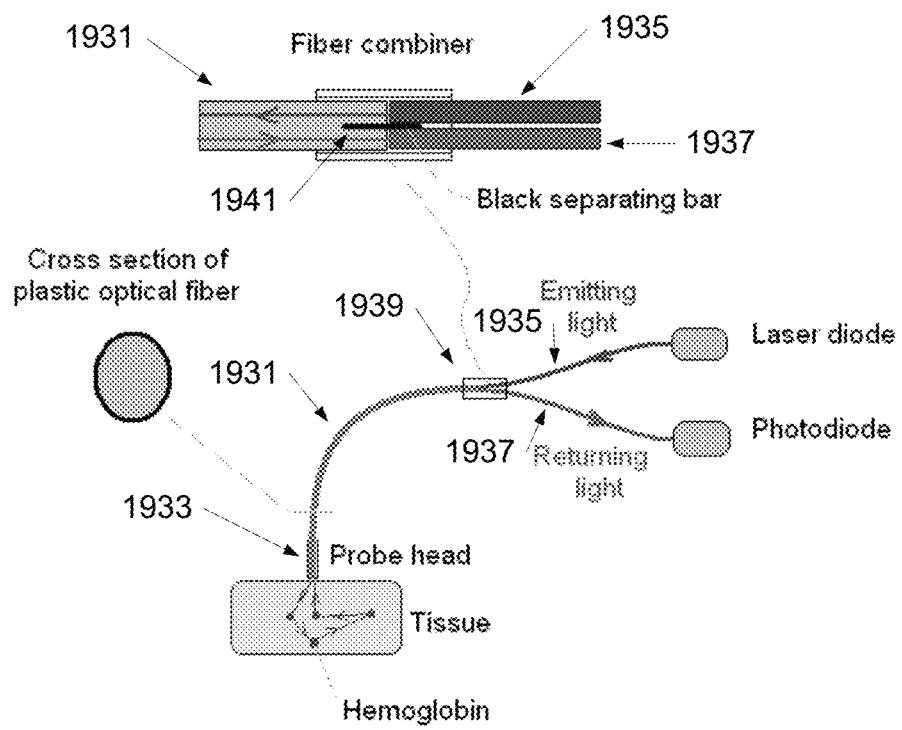
FIG. 19C shows a retractor oximeter that has a single sensor opening at the tip and a distal end of a single optical fiber connected to the sensor opening, and a proximal end of the single optical fiber combined with two optical fibers by a fiber combiner.

FIG. 19C illustrates another implementation of the invention where a distal end of a single plastic optical fiber 1931 (not a bundle) is connected to an opening at the tip of a retractor (referred to as "probe head" 1933). At a proximal end of single optical fiber 1931, the fiber is connected to two separate optical fibers 1935 and 1937 by a 1-to-2 (i.e., Y-shaped) fiber combiner 1939. Typically, the fiber combiner contains a black separating bar 1941 to reduce cross talk between the emitting light and returning light at the two surfaces between the three fibers.

In the implementations shown in FIGS. 19B and 19C, the returning light is mainly light back scattered by hemoglobin in the skin and a shallow volume of tissue underneath the skin. This is because a distance between an emitting optical fiber and returning optical fiber is less than the diameter of the optical fiber bundle (e.g., 1 millimeter). The light being returned has not traveled deeply into the tissue. Therefore, the returning light carries more information about oxygen saturation level of the skin and a shallow volume of tissue underneath the skin, not a whole block of tissue deep underneath the skin. Accordingly, the implementations shown in FIGS. 19B and 19C are particularly useful in measuring oxygen saturation of a thin layer of tissue.

Figure 20:
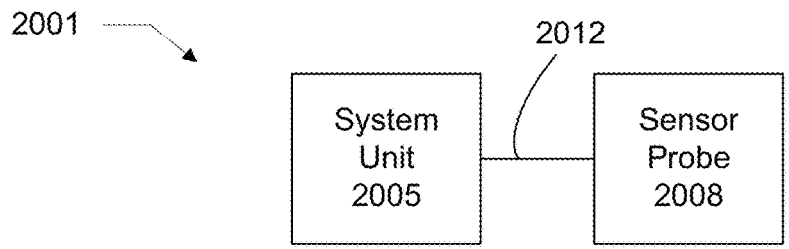
FIG. 20 shows a retractor system including a system unit and a sensor probe.

FIG. 20 shows a system 2001 for retracting a tissue and for measuring one or more parameters associated with a retracted tissue. The system 2001 contains a system unit 2005 and a sensor probe 2008 (which is a retractor having one or more sensors), which is connected to the system unit via a wired connection 2012. In one implementation, the system unit 2005 may be a controller described above and shown in FIG. 1. In another embodiment, the system unit 2005 may be a system unit described above and shown in FIG. 5A.

In FIG. 20, connection 2012 may be an electrical, optical, or another wired connection including any number of wires (e.g., one, two, three, four, five, six, or more wires or optical fibers), or any combination of these or other types of connections. In other implementations of the invention, however, connection 2012 may be wireless such as via a radio frequency (RF) or infrared communication.

Typically, the system is used by placing the sensor probe in contact or close proximity to tissue (e.g., skin) at a site where an oxygen saturation, force, or other related measurement is desired. The system unit causes an input signal to be emitted by source structures in the sensor probe into the tissue (e.g., human tissue). There may be multiple input signals, and these signals may have varying or different wavelengths. The input signal is transmitted into or through the tissue.

Then, after transmission through or reflection off the tissue, the signal is received by detector structures in the sensor probe. This received signal is received and analyzed by the system unit. Based on the received signal, the system unit determines the oxygen saturation or other parameters of the tissue and provides an output signal (e.g., a visual or audible signal).

In an implementation, the system is a tissue oximeter, which can measure oxygen saturation without requiring a pulse or heart beat. A tissue oximeter of the invention is applicable to many areas of medicine and surgery including plastic surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbance of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Various equations for self-calibration schemes are also known in the art. Self-calibration schemes are used to adjust for system factors such as source intensity, detector gain, and loss of light in the optical fibers and connectors. The self-calibration scheme may include equations discussed in U.S. Pat. Nos. 6,516,209, 6,735,458, and 6,078,833, and *New Optical Probe Designs for Absolute (Self-Calibrating) NIR Tissue Hemoglobin Measurements*, Proc. SPIE 3597, pages 618-631 (1999), which are incorporated by reference.

The attenuation ratio method may also include techniques discussed in U.S. Pat. No. 6,587,701, which is incorporated by reference. The attenuation ratio method is used to determine tissue oxygenation, hemoglobin concentration, or both. Additional detail on self-calibration schemes and attenuation ratio methods is also discussed in U.S. patent application Ser. No. 12/126,860, filed May 24, 2008, which is incorporated by reference.

Figure 21:
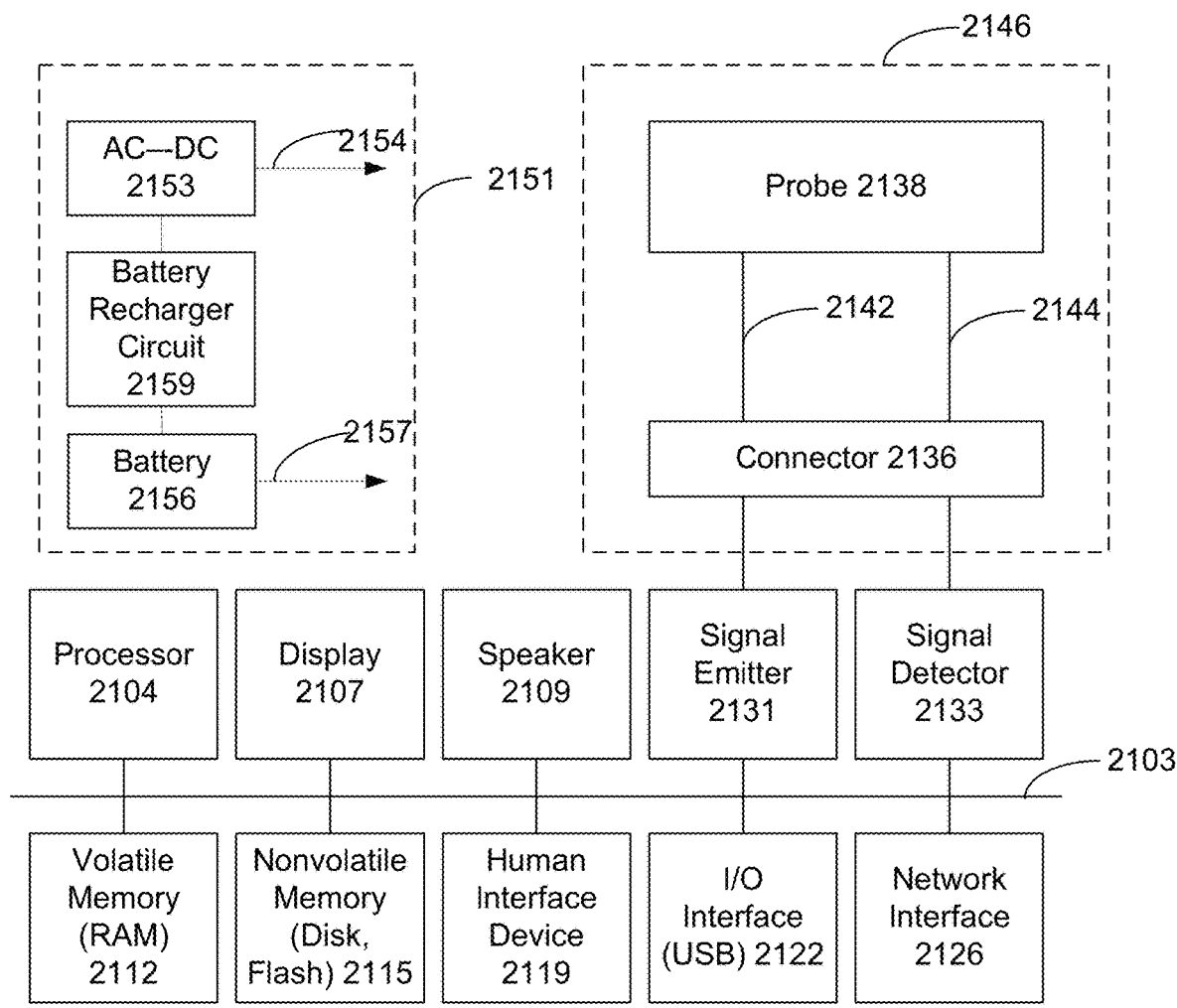
FIG. 21 shows detail of a specific implementation of the system of FIG. 20.

FIG. 21 shows a specific implementation of the system of FIG. 20, where some of the components of the system are shown in greater detail. The system unit includes a processor 2104, display 2107, speaker 2109, signal emitter 2131, signal detector 2133, volatile memory 2112, nonvolatile memory 2115, human interface device or HID 2119, I/O interface 2122 (e.g., USB), and network interface 2126. These components can be housed within a single system unit enclosure or separately. Different implementation of the system may include any number of the components described, in any combination or configuration, and may also include other components not shown.

The components are linked together using a bus 2103, which represents the system bus architecture of the system. Although this figure shows one bus that connects to each component, the busing is illustrative of any interconnection scheme serving to link the subsystems. For example, speaker 2109 could be connected to the other subsystems through a port or have an internal direct connection to processor 2104.

A sensor probe 2146 of the system includes a probe 2138 and connector 2136. The probe is connected to the connector using one or more wires 2142 and 2144. The connector removably connects the probe and its wires to the signal emitter and signal detectors in the system unit. There is one cable or set of cables 2142 to connect to the signal emitter, and one cable or set of cables 2144 to connect to the signal detector. In an implementation the cables are fiber optic cables, but in other implementations, the cables are electrical wires.

Signal emitter 2131 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 2133 is typically a photodetector capable of detecting the light at the wavelengths produced by the signal emitter.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects that a cerebral probe is connected, the system uses cerebral probe algorithms and operation. When the system detects a nerve retractor probe is connected, the system uses nerve retractor probe algorithms and operation. A system can handle any number of different types of probes. There may be different probes for measuring different parts of the body, or different sizes or versions of probe for measuring a part of the body (e.g., three different nerve retractor probe models).

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

In some applications, probe 2146 can be a handheld tool and a user moves the probe from one point to another to make measurements. In other applications, probe 2146 can be part of an endoscopic instrument or robotic instrument, or both. For example, the probe is moved or operated using a guiding interface, which may or may not include haptic technology.

In various implementations, the system is powered using a wall outlet or battery powered, or both. Block 2151 shows a power block of the system having both AC and battery power options. In an implementation, the system includes an AC-DC converter 2153. The converter takes AC power from a wall socket, converts AC power to DC power, and the DC output is connected to the components of the system needing power (indicated by an arrow 2154). In an implementation, the system is battery operated. The DC output of a battery 2156 is connected to the components of the system needing power (indicated by an arrow 2157). The battery is recharged using a recharger circuit 2159, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows 7, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
receiving from a sensor a sensor reading signal, wherein the sensor reading signal comprises a reading from an oximeter sensor, and the sensor comprises a first sensor emitter structure and a first sensor detector structure;
determining a parameter, by using the sensor reading signal from the sensor, of a tissue that is retracted by a retractor comprising the sensor;
determining if the parameter is above a first value;
producing a first control signal to alter a position of the retractor if the parameter is not above the first value, wherein the first control signal alters the position of the retractor in a first direction;
determining if the parameter is below a second value, wherein the second value is greater than the first value; and
producing a second control signal to alter a position of the retractor if the parameter is not below the second value, wherein the second control signal alters the position of the retractor in a second direction, and the second direction is opposite to the first direction.

2. The method of claim 1 wherein the sensor is a tissue oximeter and the parameter is an oxygen saturation.

3. The method of claim 2 further comprising determining a force applied to the retractor to retract the tissue.

4. The method of claim 1 wherein the tissue is a nerve and the retractor is a nerve retractor.

5. The method of claim 1 wherein the sensor is a tissue oximeter sensor which can make oxygen saturation measurements of the tissue when there is no pulse.

6. The method of claim 1 wherein the first control signal is coupled to a controller, the controller is coupled to a positioning mechanism, and the controller electronically controls the positioning mechanism to adjust a mechanical positioning of the retractor based on a reading from the sensor.

7. The method of claim 1 wherein the retractor comprises a shaft having a proximal end coupled to a positioning mechanism, a distal end comprising a tip, and the tip comprises the sensor and a retractor portion.

8. The method of claim 1 wherein the sensor comprises a second sensor detector structure.

9. The method of claim 1 wherein the sensor comprises a second sensor emitter structure.

10. The method of claim 1 wherein the sensor comprises a second sensor emitter structure and a second sensor detector structure.

11. The method of claim 1 wherein the sensor comprises a second sensor emitter structure and a second sensor detector structure, and any of the three structures are positioned in a linear arrangement.

12. A method comprising:
determining a parameter, by using an oximeter sensor, of a tissue that is retracted by a retractor comprising the oximeter sensor, wherein the oximeter sensor comprises a first source structure and first detector structure;
determining if the parameter is above a first value;
producing a control signal if the parameter is not above the first value; and
automatically adjusting, based on the control signal, a retraction force applied by the retractor onto the tissue by altering a positioning of the retractor.

13. The method of claim 12 wherein the control signal actuates a positioning mechanism that alters a positioning of the retractor.

14. The method of claim 12 wherein the oximeter sensor is a tissue oximeter sensor that can make oxygen saturation measurements of the tissue when there is no pulse.

15. The method of claim 12 wherein the sensor comprises a second detector structure.

16. The method of claim 12 wherein the sensor comprises a second source structure.

17. The method of claim 12 wherein the sensor comprises a second source structure and a second detector structure.

18. The method of claim 12 wherein the sensor comprises a second source structure and a second detector structure, and any of the three structures are positioned in a linear arrangement.

19. A method comprising:
determining a parameter, by using an oximeter sensor, of a tissue that is retracted by a retractor comprising the oximeter sensor, wherein the oximeter sensor comprises a first source structure, second source structure, first detector structure, and second detector structure;
determining if the parameter is above a first value;
producing a control signal if the parameter is above the first value; and
automatically adjusting, based on the control signal actuating a positioning mechanism that alters a positioning of the retractor, a retraction force applied by the retractor onto the tissue by altering a positioning of the retractor.

20. The method of claim 19 wherein the control signal is coupled to a controller, the controller is coupled to a positioning mechanism, and the controller electronically controls the positioning mechanism to adjust a mechanical positioning of the retractor based on a reading from the oximeter sensor.

21. The method of claim 19 wherein the oximeter sensor is a tissue oximeter sensor that can make oxygen saturation measurements of the tissue when there is no pulse.

22. The method of claim 19 wherein and any three of the first source structure, second source structure, first detector structure, and second detector structure are positioned in a linear arrangement.

23. The method of claim 19 wherein the parameter is an oxygen saturation.

24. The method of claim 19 comprising determining a force applied to the retractor to retract the tissue.

25. The method of claim 19 wherein the tissue is a nerve and the retractor is a nerve retractor.

26. The method of claim 19 wherein the control signal is coupled to a controller, the controller is coupled to the positioning mechanism, and the controller electronically controls the positioning mechanism to adjust a mechanical positioning of the retractor based on a reading from the oximeter sensor.

27. The method of claim 19 wherein the retractor comprises a shaft having a proximal end coupled to a positioning mechanism, a distal end comprising a tip, and the tip comprises the sensor and a retractor portion.

28. The method of claim 12 wherein the parameter is an oxygen saturation.

29. The method of claim 12 comprising determining a force applied to the retractor to retract the tissue.

30. The method of claim 12 wherein the tissue is a nerve and the retractor is a nerve retractor.

31. The method of claim 12 wherein the control signal is coupled to a controller, the controller is coupled to the positioning mechanism, and the controller electronically controls the positioning mechanism to adjust a mechanical positioning of the retractor based on a reading from the oximeter sensor.

32. The method of claim 12 wherein the retractor comprises a shaft having a proximal end coupled to a positioning mechanism, a distal end comprising a tip, and the tip comprises the sensor and a retractor portion.

* * * * *